US009572898B2

(12) United States Patent
Sabatino et al.

(10) Patent No.: US 9,572,898 B2
(45) Date of Patent: Feb. 21, 2017

(54) FUNCTIONALIZED FLUORINE CONTAINING PHTHALOCYANINE MOLECULES

(71) Applicant: Seton Hall University, South Orange, NJ (US)

(72) Inventors: David Sabatino, Newark, NJ (US); Sergiu M. Gorun, Montclair, NJ (US); Emily Borland, Plainsboro, NJ (US); Hemantbhai Patel, Piscataway, NJ (US); Pradeepkumar Patel, Gujarat (IN); Erik Nathaniel Carrión, West Orange, NJ (US)

(73) Assignee: Seton Hall University, South Orange, NJ (US)

( * ) Notice: Subject to any disclaimer, the term of this patent is extended or adjusted under 35 U.S.C. 154(b) by 0 days.

(21) Appl. No.: 14/481,488

(22) Filed: Sep. 9, 2014

(65) Prior Publication Data
US 2015/0071862 A1 Mar. 12, 2015

Related U.S. Application Data

(60) Provisional application No. 61/875,987, filed on Sep. 10, 2013, provisional application No. 61/875,525, filed on Sep. 9, 2013.

(51) Int. Cl.
*A61K 49/00* (2006.01)
*C07K 7/08* (2006.01)
*C12N 15/113* (2010.01)
*A61K 41/00* (2006.01)
*C12N 15/11* (2006.01)
*A61K 47/48* (2006.01)

(52) U.S. Cl.
CPC ....... *A61K 49/0036* (2013.01); *A61K 41/0071* (2013.01); *A61K 47/48092* (2013.01); *A61K 47/48246* (2013.01); *C07K 7/08* (2013.01); *C12N 15/111* (2013.01); *C12N 15/113* (2013.01); *C12N 2310/351* (2013.01); *C12N 2320/30* (2013.01)

(58) Field of Classification Search
None
See application file for complete search history.

(56) References Cited

U.S. PATENT DOCUMENTS 9,150,431 B1 10/2015 Gorun et al.

OTHER PUBLICATIONS

Das et al., Perfluoroisopropyl Zinc Phthalocyanines Conjugated with Deoxyribonucleosides: Synthesis, Photophysical Properties and In Vitro Photodynamic Activities;, Eur J Org Chem, 2878-2884, 2010.*
Katanasaka et al., Cancer antineovascular therapy with liposome drug delivery systems targeted to BiP/GRP78, International Journal of Cancer, vol. 127, pp. 1685-2698, 2010.*
Pan et al., HSP70 and GRP78 Induced by Endothelin-1 Pretreatment Enhance Tolerance to Hypoxia in Cultured Neonatal Rat Cardiomyocytes; J Cardiovasc Pharmacol, vol. 44, pp. S117-S120, 2004.*
Calin, M.A. et al. (2006) Photodynamic therapy in oncology, J. Optoelect. Adv. Mat. 8, 1173-1179; Thierry Patrice. Photodynamic Therapy; Royal Society of Chemistry, 2004.
Ishii, K. (2012) Functional singlet oxygen generators based on phthalocyanines, Coord. Chem. Rev. 256, 1556-1568.
Josefsen, L.B. et al. (2012) Unique diagnostic and therapeutic roles of porphyrins and phthalocyanines in photodynamic therapy, imaging and theranostics, Theranostics 2, 916-966.
Master, A. et al. (2013) A cell-targeted photodynamic nanomedicine strategy for head and neck cancers, Mol Pharm. 10, 1988-1997.
Sibrian-Vazquez, M., et al., Synthesis and Properties of Cell-Targeted ZN(11)—Phthalocyanine—Peptide Conjugates, Bioconjugate Chem. 2007, 18, 410-420.
Ranyuk, Elena, et al., Phthalocyanine—Peptide Conjugates: Receptor-Targeting Bifunctional Agents for Imaging and Photodynamic Therapy, Journal of Medicinal Chemistry, 2013, 56, 1520-1534.
Ongarora, Benson G., et al., Phthalocyanine—Peptide Conjugates for Epidermal Growth Factor Receptor Targeting, Journal of Medicinal Chemistry, 2012, 55, 3725-3738.
Huang, Lei, et al., Photochemical DNA cleavage by novel water-soluble sulfonated dihydroxy phosphorus(V) tetrabenzotriazacorrole, Biorganic & Medicinal Chemistry Letters 18 (2008) 2152-2155.
Kuznetsova, A. A., et al., DNA—binding and oxidative properties of cationic phthalocyanines and their dimeric complexes with anionic phthalocyanines covalently linked to oligonucleoties, Journal of Biomolecular Structure & Dynamics, Jan. 2009.
Erdem, S. S., et al., Mono-amine Functionalized Phthalocyanines: Microwave-Assistsed Solid-Phase Synthesis and Bioconjugation Strategies, J. Org. Chem. 2009, 74, 9280-9286.

(Continued)

*Primary Examiner* — Addison D Ault
(74) *Attorney, Agent, or Firm* — Lerner, David, Littenberg, Krumholz & Mentlik, LLP

(57) ABSTRACT

Functionalized fluorine containing phthalocyanine molecules, methods of making, and methods of use in diagnostic applications and disease treatment are disclosed herein. In some embodiments, the fluorine containing phthalocyanine molecules are functionalized with a reactive functional group or at least one cancer-targeting ligand (CTL). The CTL can facilitate more efficient binding and/or internalization to a cancer cell than to a healthy cell. The CTL can inhibit expression of oncoprotein in some embodiments. The pthalocyanine moiety can be used in diagnostic applications, such as fluorescence labeling of a cancer cell, and/or treatment applications, such as catalyzing formation of a reactive oxygen species (ROS) which can contribute to cell death of a cancer cell.

9 Claims, 6 Drawing Sheets

(56) References Cited

OTHER PUBLICATIONS

Figure 2A:
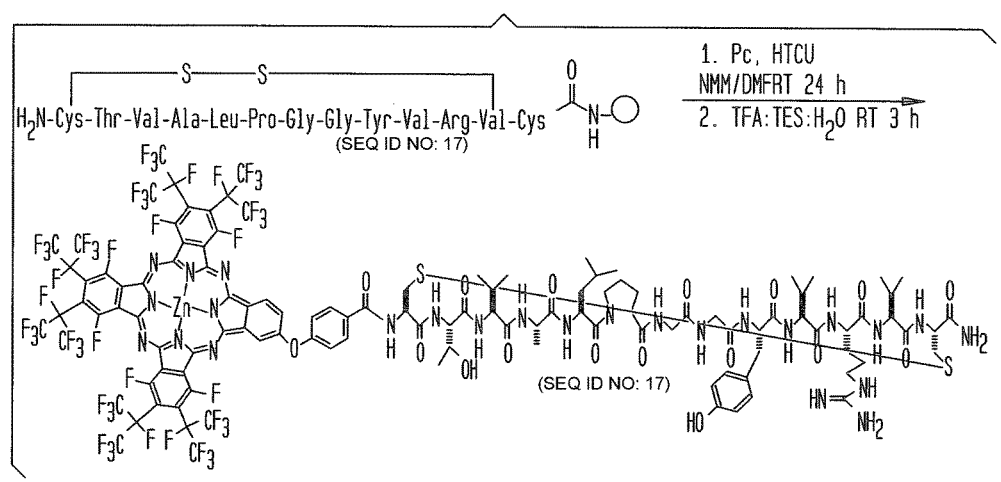

Nesterova, I. V. et al., Metallo-Phthalocyanine Near-IR Fluorophores: Oligonucleotide Conjugates and Their Applictaions in PCR Assays, Bioconjugate Chem., 2007, 18, 2159-2168.

Maina, Anthony, et al., Solid-Phase Synthesis, Characterization and RNAi Activity of Branch and Hyperbranch siRNAs, Bioorganic Med. Chem. Lett., (2013), 5270-5274.

Nesterova, I.V., et al., Phthalocyanine Dimerization-Based Molecular Beacons Using Near-IR Fluorescence, Journal American Chemical Society, 2009, 131, 2432-2433.

Ke, M.R. et al., A Phthalocyanine--Peptide Conjugate with High In Vitro Photodynamic Activity and Enhanced In Vivo Tumor-Retention Property, Chem., Eur. J. 2012, 18, 4225-4233.

Jerry Ting and Amy S. Lee, Human Gene Encoding the 78,000-Dalton Glucose-Regulated Protein and Its Pseudogene: Structure, Conservation, and Regulation, DNA, vol. 7, 1988, 275-286.

Patel, P. et al., Chemically robust fluoroalkyl phthalocyanine—oligonucleotide bioconjugates and their GRP78 oncogene photocleavage activity, Chem Commun, 2014, 50 6309-6311.

Berge, S. M., et al., Pharmaceutical Salts, Journal of Pharmaceutical Sciences, Jan. 1977, vol. 66, No. 1.

Lau, Janet T. F., et al., A Dual Activable Photosensitizer toward Targeted Photodynamic Therapy, Journal of Medicinal Chemistry, 2014, 57, 4088-4097.

Pfaffenbach, Kyle T. and Lee, Amy S., The critical role of GRP78 in physiologic and pathologic stress, Current Opinion in Cell Biology, 2011, 23:150-156.

Ni, Min, et al., Beyond the endoplasmic reticulum: atypical GRP78 in cell viability, signalling and therapeutic targeting, Biochem. J. (2011) 434, 181-188.

J. Joseph and G. Boomadevi Janaki, Synthesis, structural characterization and biological studies of copper complexes with 2-aminobenzothiazole derivatives, Journal of Molecular Structure, 1063 (2014) 160-169.

Liu, Ying, et al., Mechanistic Studies of a Peptidic GRP78 Ligand for Cancer Cell-Specific Drug Delivery, Molecular Pharmaceutics, (2007) vol. 4, No. 3, 435-447.

Kim Youngsoo, et al., Targeting Heat Shock Proteins on Cancer Cells: Selection, Characterization, and Cell-Penetrating Properties of a Peptidic GRP78 Ligand, Biochemistry 2006, 45, 9434-9444.

Wey Shiuan, et al., Inducible knockout of GRP78/BiP in the hematopoietic system supresses Pten-null leukemogenesis and AKT oncogenic signaling, Blood, Jan. 2012, vol. 119, No. 3.

Chang, Yu-Jia, et al., GRP78 Knockdown Enhances Apoptosis via the Down-regulation of Oxidative Stress and Akt Pathway after Epirubicin Treatment in Colon Cancer DLD-1 Cells, PLoS One, Apr. 2012, vol. 7, Issue 4, e35123.

Zhang, Lu-Hua, et al., Association of elevated GRP78 expression with increased astrocytoma malignancy via Akt and ERK pathways, Brain Research 1371 (2011) 23-31.

Tanimoto, Ryuta, et al., Down-regulation of BiP/GRP78 sensitizes resistant prostate cancer cells to gene-therapeutic overexpression of REIC/Dkk-3, Int. J. Cancer: 126, 1562-1569 (2010).

Alhoot, Mohammed Abdelfatah, et al., RNA Interference Mediated Inhibition of Dengue Virus Multiplication and Entry in HepG2 Cells, PLoS One, Mar. 2012, vol. 7, Issue 3, e34060.

Burrows, C. J., and Muller, J. G., Oxidative Nucleobase Modifications Leading to Strand Scission, Chem. Rev. 1998, 98, 1109-1151.

Tchou, Julia, et al., Substrate Specificity of Fpg Protein, The Journal of Biological Chemistry, (1994), vol. 269, No. 21, Issue of May 27, 15318-15324.

St Denis, T.G. and Hamblin, Michael R., Synthesis, bioanalysis and biodistribution of photosensitizer conjugates for photodynamic therapy, Bioanalysis (2013) 5(9), 1099-1114.

Joseph, S. C., et al., Synthesis, characterization, and biological activity of poly(arginine)-derived cancer-targeting peptides in HepG2 liver cancer cells, J. Pept. Sci., 2014, 20: 736-745.

Sergiu M. Gorun, David Sabatino et al., Chemically robust fluoroalkyl phthalocyanine—oligonucleotide bioconjugates and their GRP78 oncogene photocleavage activity, Royal Society of Chemistry, Chem. Commun., 2014, 50, 6309-6311.

Dalton Transactions, An international journal of inorganic chemistry, www.rsc.org/dalton, vol. 44, No. 15, Apr. 2015.

Andrei Loas, Robert Gerdes, et al., Broadening the reactivity spectrum of a phthalocyanine catalyst while suppressing its nucleophilic, electrophilic and radical degradation pathways, Dalton Transactions, 2011, 40, 5162.

Lapok, L., Lener, M., et al, Structures and Redox Characteristics of Electron-Deficient Vanadyl Phthalocyanines, Inorganic Chemistry, American Chemical Society, 2011, 4086-4091.

Schlothauer, J., Hackbarth, S., et al. Time-resolved singlet oxygen luminescence detection under Dhotodynamic therapy relevant conditions: comparison of ex vivo application of two photosensitizer formulations, Journal of Biomedical Optics, Nov. 2012, vol. 17 (11).

Robert P. Hammer, Clyde V. Owens, et al., Asymmetrical, Water-Soluble Phthalocyanine Dyes for Covalent Labeling of Oligonucleotides, Bioconjugate Chem., 2002, 13, 1244-1252.

Li, L, Luo, Z, et al, Enhanced Photodynamic Efficacy of Zinc Phthalocyanine by Conjugating to Heptalysine, Bioconjugate Chemistry, ACS Publications, 2012, pp. 2168-2172.

Kuznetsova, A., Chernonosov, A., et al, Kinetic Study of DNA Modification by Phthalocyanine Derivative of the Oligonucleotide, Hindawi Publishing Corporation, Bioinorganic Chemistry and Applications, vol. 2006, Article ID 23560, pp. 1-10, DOI 10.1155/BCA/2006/23560.

Macaskill, A., Chernonosov, A. A., et al., Quantitative surface-enhanced resonance Raman scattering of phthalocyanine-labelled oligonucleotides, Nucleic Acids Research, 2007, vol. 35, No. 6.

Ali, H., Ait-Mohand, S., et al., Phthalocyanine-Peptide Conjugates via Palladium-Catalyzed Cross-Coupling Reactions, The Journal of Organic Chemistry, ACS Publications, 2011.

Sharman, W., Van Lier, J., Synthesis and Photodynamic Activity of Novel Asymmetrically Substituted Fluorinated Phthalocyanines, Bioconjugate Chem. 2005, 16, 1166-1175.

Kopecky, K., Novakova, V., et al., Solid-Phase Synthesis of Azaphthalocyanine-Oligonucleotide Conjugates and Their Evaluation As New Dark Quenchers of Fluorescence, Bioconjugate Chem., vol. 21, No. 10, 2010, 1872-1879.

Qiu, T., Xu, X., et al., Novel perfluoralkyl phthalocyanine metal derivatives: Synthesis and photodynamic activities, Dyes and Pigments 83, 2009, 127-133.

Moons, H. Lapok, L., et al., Synthesis, X-Ray Structure, Magnetic Resonance, and DFT Analysis of a Soluble Copper (II) Phthalocyanine Lacking C—H Bonds, Inorganic Chemistry, 2010, 49, 8779-8789.

Drozd, D., Szczubialka, K, et al., Visible light induced photosensitized degradation of Acid Orange 7 in the suspension of bentonite intercalated with perfluoroalkyl perfluoro phthalocyanine zinc complex, Applied Catalysis B: Environmental, 125, 2012, 35-40.

Keil, C., Tsaryova, C., et al, Growth and characterization of thin films prepared from perfluoro-isopropyl-substituted perfluorophthalocyanines, Thin Sold Films, 517, 2009, 4379-4384.

Minnes, R., Weitman, H., et al., Enhanced Acidity, Photophysical Properties and Liposome Binding of Perfluoroalkylated Phthalocyanines Lacking C-H Bonds, Photochemistry and Photobiology, 2006, 82, 593-599.

Bench, B., Beveridge, A., et al., Perfluoroalkyl, Phthalocyanines, Angew. Chem. Int. Ed., 2002, 41, No. 5, Wiley-VCH Verlag GmbH.

Keizer, S. P., Han, W., Stillman, M., Photochemically-Induced Radical Reactions of Zinc Phthalocyanine, Inorganic Chemistry, vol. 41, No. 2, 2002. 353-358.

Keizer, S. P., Mack, J., Spectroscopy and Electronic Structure of Electron Deficient Zinc Phthalocyanines, J. Am. Chem. SOC., 2003, 125, 7067-7085.

Beveridge, A., Bench, B. et al., Evaluation of Photodynamic Therapy Agents through Transient Grating Measurements, J. Phys. Chem. A. 2003, 107, 5138-5143.

* cited by examiner

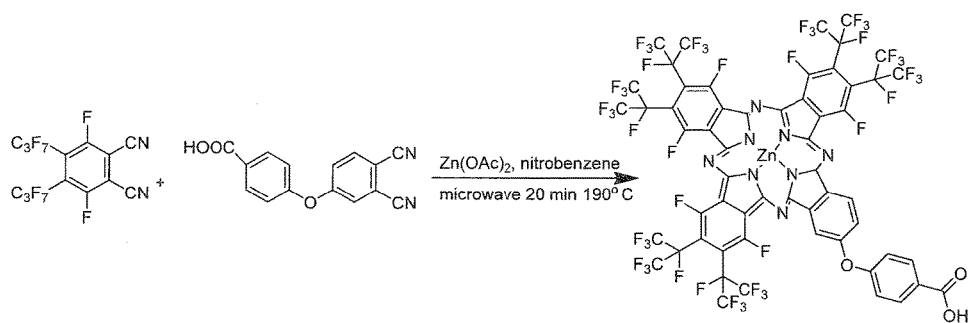
Figure 1A – Synthesis of a carboxy functionalized fluorine-containing phthalocyanine
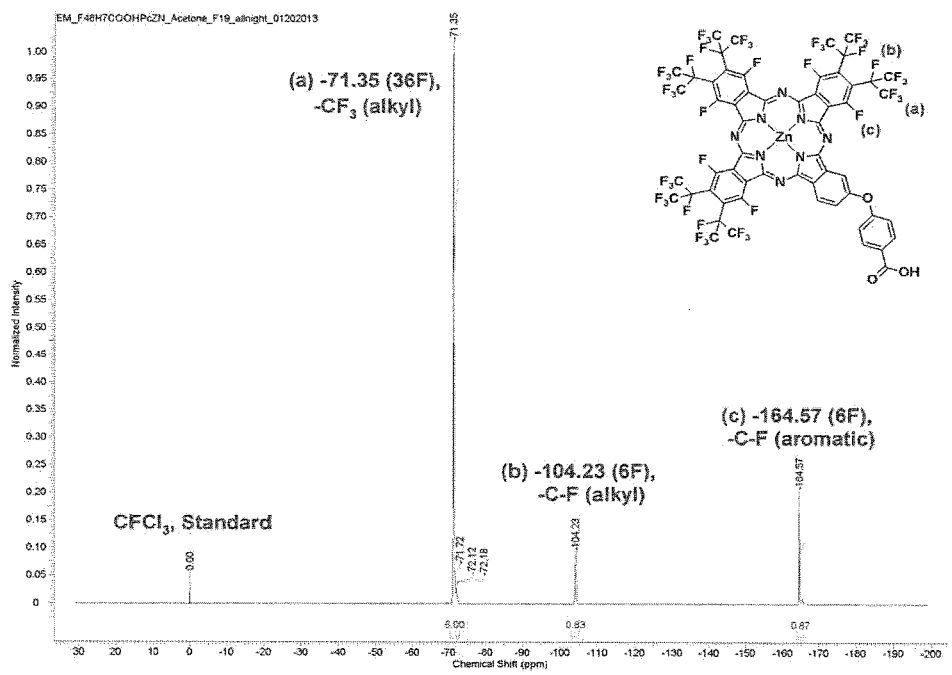
Figure 1B – $^{19}$F NMR of a carboxy functionalized fluorine-containing Phthalocyanine.

SYNTHESIS OF A PEPTIDE-FUNCTIONALIZED FLUORINE CONTAINING PHTHALOCYANINE.

HIGH-RESOLUTION MASS SPECTRA OF A PEPTIDE-FUNCTIONALIZED FLUORINE CONTAINING PHTHALOCYANINE.
TOP SPECTRA: OBSERVED: 3146.475 g/mol. BOTTOM SPECTRA: CALCULATED: 3146.591 g/mol.

SYNTHESIS OF AN OLIGONUCLEOTIDE-FUNCTIONALIZED FLUORINE CONTAINING PHTHALOCYANINE.

LCMS SPECTRA OF AN OLIGONUCLEOTIDE-FUNCTIONALIZED FLUORINE CONTAINING PHTHALOCYANINE. LEFT SPECTRA: LC SPECTRA. RIGHT SPECTRA: MS SPECTRA: OBS. 7412.2 g/mol; CALCULATED: 7411.6 g/mol (NOT SHOWN).

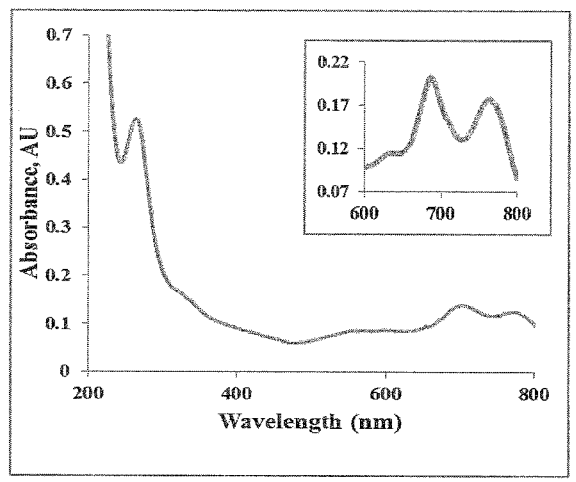
Figure 4A - UV-Vis electronic absorption spectra of an oligonucleotide-functionalized fluorine containing phthalocyanine.
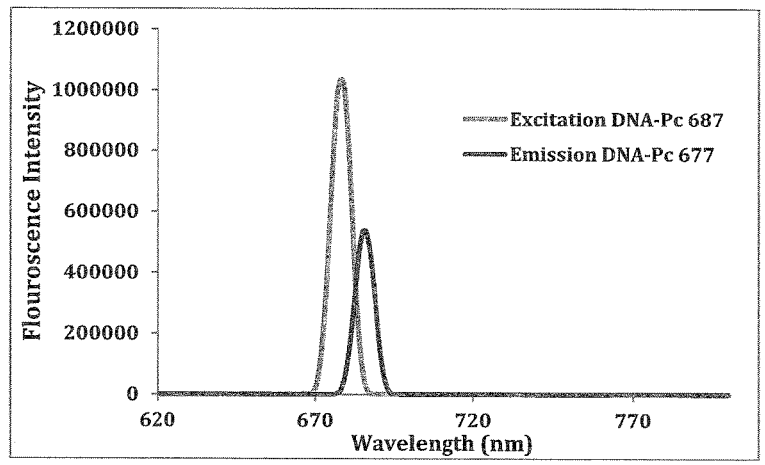
Figure 4B - Fluorescence spectra of an oligonucleotide-functionalized fluorine containing phthalocyanine.

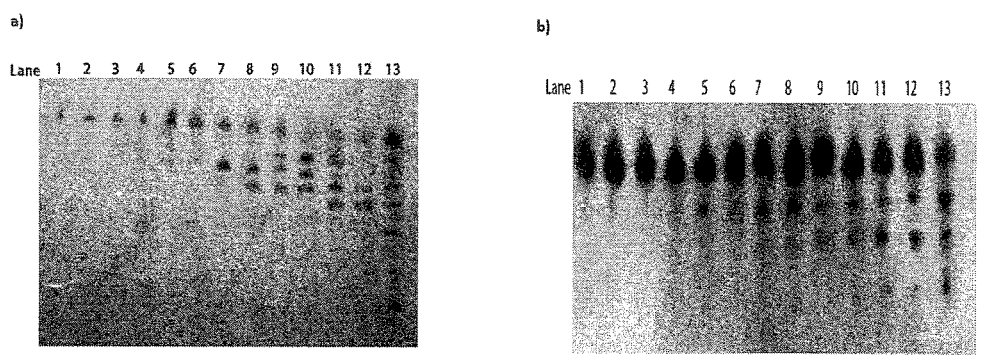
Figure 5A,B - 24% PAGE for the photo-oxidation and piperidine cleavage pattern of a) Pc-CTO:DNA and b) Pc-CTO:RNA. Lane 1: light, but no $O_2$.
Lane 2: no light, but with $O_2$. Lanes 3-13, time points from 0-12 hrs.

FUNCTIONALIZED FLUORINE CONTAINING PHTHALOCYANINE MOLECULES

CROSS-REFERENCE TO RELATED APPLICATIONS

The present application claims the benefit of the filing date of U.S. Provisional Patent Application No. 61/875,525, filed Sep. 9, 2013, and U.S. Provisional Patent Application No. 61/875,987, filed Sep. 10, 2013, the disclosures of which are hereby incorporated herein by reference.

SEQUENCE LISTING

The instant application contains a Sequence Listing which has been submitted electronically in ASCII format and is hereby incorporated by reference in its entirety. Said ASCII copy, created on Nov. 18, 2014, is named SETON3.0E-006 (E)_SL.txt and is 8,066 bytes in size.

FIELD OF THE INVENTION

Functionalized fluorine containing phthalocyanine molecules, methods of making the same, and methods of use in diagnostic applications and disease treatment are disclosed herein.

BACKGROUND OF THE INVENTION

The application of photodynamic therapy (PDT) in oncology relies upon the use of a photosensitizer to produce reactive oxygen species (ROS), such as singlet oxygen, $^1O_2$, to destroy cancer cells by terminally modifying the biomolecules they interact with [Calin, M. A. et al. (2006) Photodynamic therapy in oncology, J. Optoelect. Adv. Mat. 8, 1173-1179; Thierry Patrice. Photodynamic Therapy; Royal Society of Chemistry, 2004].

A photosensitizing agent, such as ground state, singlet phthalocyanine (Pc), $^1Pc$, absorbs light to generate a triplet excited state, $^3Pc$, that in turn transfers its energy to ground state triplet oxygen, $^3O_2$, to produce excited state singlet oxygen, $^1O_2$, and regenerate the $^1Pc$ [Ishii, K. (2012) Functional singlet oxygen generators based on phthalocyanines, Coord. Chem. Rev. 256, 1556-1568]. Pcs absorb light strongly in the red and near-infrared regions of the electromagnetic spectrum, 600-1000 nm, favorable for benign tissue penetration. This effect stimulates $^1O_2$ production in an aerobic tumor microenvironment, ultimately leading to programmed cancer cell death [Josefsen, L. B. et al. (2012) Unique diagnostic and therapeutic roles of porphyrins and phthalocyanines in photodynamic therapy, imaging and theranostics, Theranostics 2, 916-966].

Cancer-targeting Pc photosensitizers have been shown to enhance the efficiency of the PDT response in tumor cells while reducing their side effects [(a) Master, A. et al. (2013) A cell-targeted photodynamic nanomedicine strategy for head and neck cancers, Mol Pharm. 10, 1988-1997, (b) Sibrian-Vazquez, M. et al. (2007) Synthesis and properties of cell-targeted Zn(II)-phthalocyanine-peptide conjugates, Bioconjug Chem. 18, 410-420, (c) Ranyuk, E. et al. (2013) Phthalocyanine-peptide conjugates: receptor-targeting bifunctional agents for imaging and photodynamic therapy, J Med Chem. 56, 1520-1534, (d) Ongarora, B. G. et al. (2012) Phthalocyanine-peptide conjugates for epidermal growth factor receptor targeting, J Med Chem. 55, 3725-3738, (e) Ke, M. R. et al. (2012) A phthalocyanine-peptide conjugate with high in vitro photodynamic activity and enhanced in vivo tumor-retention property, Chemistry 18, 4225-4233, (f) Huang, L. et al. (2008) Photochemical DNA cleavage by novel water-soluble sulfonated dihydroxy phosphorus(V) tetrabenzotriazacorrole, Bioorg Med Chem Lett. 18, 2152-2155, (g) Kuznetsova, A. A. et al. (2008) DNA-binding and oxidative properties of cationic phthalocyanines and their dimeric complexes with anionic phthalocyanines covalently linked to oligonucleotides, J Biomol Struct Dyn. 26, 307-320, (h) Erdem, S. S. et al. (2009) Mono-amine functionalized phthalocyanines: microwave-assisted solid-phase synthesis and bioconjugation strategies J Org Chem. 74, 9280-9286, (i) Nesterova, I. V. et al. (2007) Metallo-phthalocyanine near-IR fluorophores: oligonucleotide conjugates and their applications in PCR assays, Bioconj Chem. 18, 2159-2168].

Diagnostic applications of a Pc photosensitizer relies on its ability to absorb and emit light in the visible/near infrared region (400-900 nm) for instrumental detection [Nesterova, I. V. et al. (2009) Phthalocyanine Dimerization-Based Molecular Beacons Using Near-IR Fluorescence, J. Am. Chem. Soc. 131, 2432-2433] and diagnosis of a disease state [Master, A. et al. (2014) A Cell-Targeted Photodynamic Nanomedicine Strategy for Head and Neck Cancers, Mol. Pharm. 10, 1988-1997].

Despite the above described advances in the art, still further improvements in the Pcs and their methods of use in diagnostic applications and disease treatment would be desirable.

SUMMARY OF THE INVENTION

Functionalized fluorine containing phthalocyanine molecules, methods of making, and methods of use in diagnostic applications and disease treatment are disclosed herein. In some embodiments, a functionalized fluorine containing phthalocyanine represented by Formula (I):

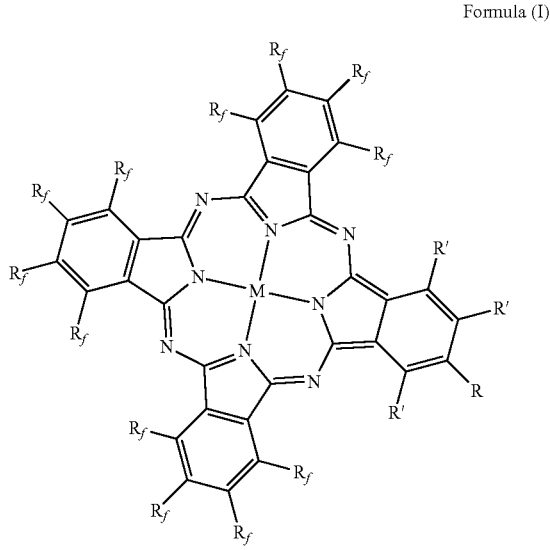

Formula (I)

In some embodiments, each Rf can be independently selected from the group consisting of a fluorine atom, a fluorocarbon group containing from 1 to 18 carbon atoms, a fluorine containing group, a non-fluorine containing group, and combinations thereof.

In some embodiments, at least one Rf includes a fluorine atom

In some embodiments, each R' independently selected a fluorine containing group, a hydrogen atom, and combinations thereof.

In some embodiments, M can be one or more of a metal atom, a non-metal atom, a metal ion, a non-metal ion, at least one of a metal atom or non-metal atom coupled to at least one axial ligand, at least one of a metal or non-metal ion coupled to at least one axial ligand.

In some embodiments, R can includes at least one of a reactive functional group or at least one cancer-targeting ligand (CTL).

In some embodiments, each R' can be a hydrogen atom.

In some embodiments, the reactive functional group is selected from the group consisting of a carboxylic acid group, an aldehyde group, an amino group, a hydrazine group, an alkyne, alkene or a diene group an azido group, an isocyanate group, an acyl haldide, a hydroxide, a thiol, a nitro, a halogen, an amide or combinations thereof.

In some embodiments, the at least one CTL is selected from the group consisting of a cancer-targeting protein/peptide (CTP), a cancer-targeting carbohydrate, a cancer-targeting lipid, a cancer-targeting oligosaccharide, a cancer-targeting oligonucleotide (CTO), a cancer-targeting small molecule and combinations thereof.

In some embodiments, the at least one CTL can be selected from the group consisting of the CTP having a peptide selected from SEQ ID NO: 17-41, and the CTO having an oligonucleotide selected from SEQ ID NO: 1-16.

In some embodiments, the at least one CTL can include at least one of a first oligonucleotide or a second oligonucleotide, wherein a second oligonucleotide, when present, is complementary or non-complementary to the first oligonucleotide.

A functionalized fluorine containing phthalocyanine can be included in a pharmaceutical composition.

In some embodiments, a pharmaceutical composition can include a functionalized fluorine containing phthalocyanine and a pharmaceutical acceptable carrier, wherein R includes the at least one cancer-targeting ligand (CTL).

In some embodiments, the at least one CTL can be selected from the group consisting of a cancer-targeting protein/peptide (CTP) having a peptide selected from SEQ ID NO: 17-41, and a cancer-targeting oligonucleotide (CTO) having an oligonucleotide selected from SEQ ID NO: 1-16.

In some embodiments, the at least one CTL comprises can include a cancer-targeting oligonucleotide (CTO), wherein the CTO further comprises at least one of a first oligonucleotide or a second oligonucleotide, wherein the second oligonucleotide, when present, is complementary or non-complementary to the first oligonucleotide.

In some embodiments, a method of oncogene silencing can include binding the at least one CTL of a pharmaceutical composition to an oncogene to limit the expression of an oncoprotein, wherein at least one CTL includes a cancer-targeting oligonucleotide (CTO).

In some embodiments, the CTO includes an oligonucleotide selected from SEQ ID NO: 1-16.

In some embodiments, the oligonucleotide can include at least one of a first oligonucleotide or a second oligonucleotide, wherein the second oligonucleotide, when present, is complementary or non-complementary to the first oligonucleotide.

In some embodiments, a method of targeting a cancer cell can include binding the at least one CTL of the pharmaceutical composition of claim 7 to a receptor on a cancer cell, wherein at least one CTL includes a cancer-targeting protein/peptide (CTP), and wherein the CTP binds and internalizes more efficiently within the cancer cell than to a healthy cell.

In some embodiments, the CTP includes a peptide selected from SEQ ID NO: 17-41.

In some embodiments, a diagnostic method can include binding the at least one CTL of the pharmaceutical composition of claim 7 to a target, wherein the at least one CTL is selected from the group of a cancer-targeting oligonucleotide (CTO), a cancer-targeting protein/peptide (CTP), and combinations thereof; illuminating the functionalized fluorine containing phthalocyanine with electromagnetic radiation having a wavelength ranging from about 600 nm to about 1000 nm; and detecting electromagnetic radiation emitted by the illuminated perfluoro-phthalocyanine.

In some embodiments, a method for chemically modifying a target can include binding the at least one CTL of the pharmaceutical composition of claim 7 to a target, wherein at least one CTL is selected from the group of a cancer-targeting oligonucleotide (CTO), a cancer-targeting protein/peptide (CTP), and combinations thereof; irradiating the functionalized fluorine containing phthalocyanine with electromagnetic radiation to form reactive oxygen species (ROS); and chemically modifying the target with the ROS.

In some embodiments, chemical modification by the ROS contributes to cell death.

Other and further embodiments of the present invention are discussed herein.

BRIEF DESCRIPTIONS OF THE DRAWINGS

These and other features of the invention will become more apparent from the following description in which reference is made to the appended drawings directed to various embodiments of the present invention, wherein:

FIGS. 1A-B depicts synthesis and characterization data for a carboxy functionalized fluorine containing phthalocyanine molecule in accordance with some embodiments of the present invention.

Figure 2B:
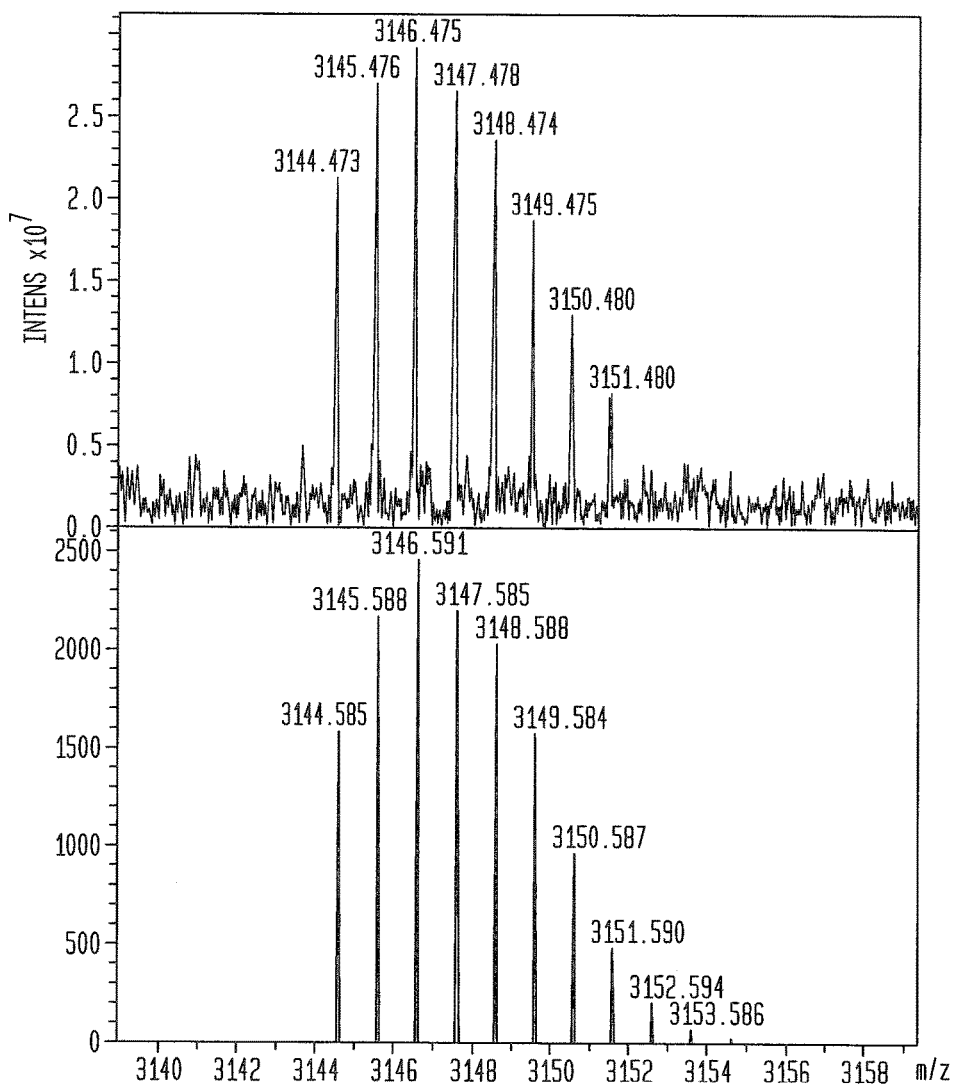

FIGS. 2A-B depicts synthesis and characterization data for a peptide functionalized fluorine containing phthalocyanine molecule in accordance with some embodiments of the present invention. FIG. 2A discloses SEQ ID NO: 17.

Figure 3A:
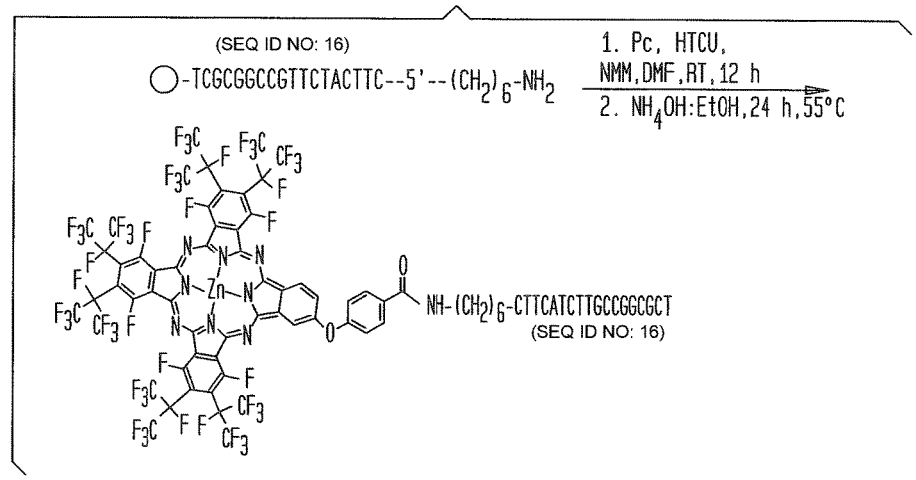
Figure 3B:
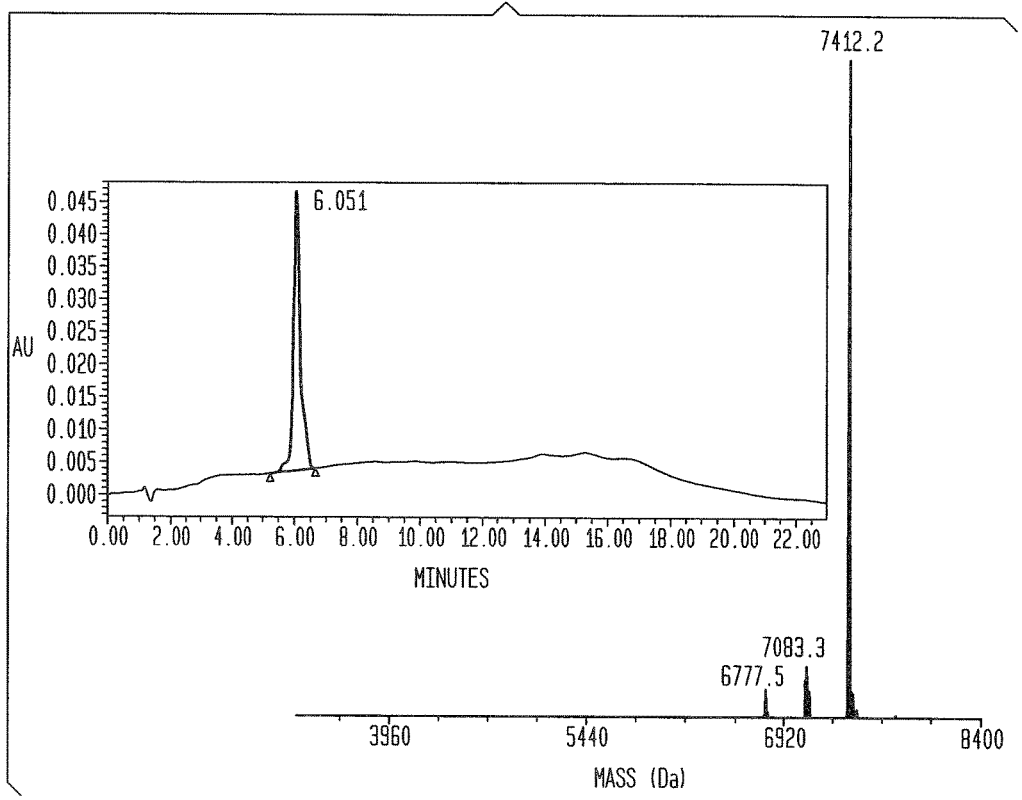

FIGS. 3A-B depict synthesis and characterization data for an oligonucleotide functionalized fluorine containing phthalocyanine molecule in accordance with some embodiments of the present invention. FIG. 3A discloses SEQ ID NO: 16 twice.

FIGS. 4A-B depicts absorption and emission data for an oligonucleotide functionalized fluorine containing phthalocyanine molecule in accordance with some embodiments of the present invention.

FIGS. 5A-B depict fragmentation patterns of target sequences following photo-oxidation by an oligonucleotide functionalized fluorine containing phthalocyanine molecule in accordance with some embodiments of the present invention.

DETAILED DESCRIPTION

Functionalized fluorine containing phthalocyanine molecules, methods of making the same, and methods of use in diagnostic applications and disease treatment are disclosed herein. The molecules of the present invention may have improved specificity and localization to tumors. The molecules of the present invention may have improved resistance to reactive oxygen species, such as those formed during photodynamic therapy (PDT).

In the following description, numerous specific details are set forth to provide a thorough understanding of the invention. However, a person skilled in the art will understand, given the context that circumstances exist in which the invention may be practiced without specific preferred features. In the following description reference is made to certain terms of the art.

As used herein, "fluorine containing phthalocyanines" are a group of photosensitizer compounds having the phthalocyanine ring system up to all their C—H bonds substituted with C—F bonds. A fluorine containing phthalocyanine where all C—H bonds are substituted with C—F bonds may be referred to as a 'perfluoro-phthalocyanine'. Phthalocyanines are azaporphyrin analogs consisting of four benzoindole groups connected by nitrogen bridges in a 16-membered ring of alternating carbon and nitrogen atoms (i.e., $C_{32}H_{16}N_8$) which form stable chelates with metal and metalloid cations. In these compounds, the ring center, or a location above the ring center is occupied by an "M" group as defined herein which includes in some embodiments a metal ion that may, depending on the ion, carry one or two extra ligands. In addition, the ring periphery may be either unsubstituted or substituted. Phthalocyanines strongly absorb clinically useful red or near IR radiation with absorption peaks in between about 600 and about 1000 nm, which potentially allows the light to deeply penetrate tissues without any damaging effects from the radiation.

As used herein, "nucleotides" are individual units consisting of a heterocyclic base covalently bonded to a 5-carbon sugar. Nucleotides have a phosphorus moiety covalently bonded to the furanose sugar moiety of the nucleoside at either the 3' or the 5' position of the sugar. The base is any heterocyclic base capable of Watson-Crick base pairing and includes any one of the naturally occurring purine and pyrimidine bases, adenine (A), thymine (T), cytosine (C), guanine (G) and uracil (U), but also any modified or analogous forms thereof. Representative examples of un-natural bases that are capable of forming base-pairing relationships include aza and deaza pyrimidine analogues, aza and deaza purine analogues, and other heterocyclic base analogues, wherein one or more of the ring atoms and functional groups of the purine and pyrimidine rings have been substituted by heteroatoms, e.g., fluorine, oxygen, sulfur, and the like. Preferably, un-natural bases include, but are not limited to, inosine, 2,6-diaminopurine, 5-methylcytosine, 5-fluorocytosine, 5-bromocytosine, 5-iodocytosine, isocytosine, $N_4$-methylcytosine, 5-iodouracil, 5-fluorouracil, 4-thiouracil, 4-thiothymine, 2-thiouracil, 2-thiothymine, 7-deaza-adenine, $N_6$-methyladenine, isoguanine, 7-deazaguanine, and 6-thioguanine. The 5-carbon sugar will typically be a naturally occurring sugar such as 2-deoxyribose, or ribose. Examples of modifications to the 5-carbon sugar include 2'-methoxynucleosides, 2'-fluoronucleosides, 2'-arabinonucleosides, 2'-selenonucleosides and locked nucleosides.

As used herein, "oligonucleotides" are polymers of at least two nucleoside units, wherein each of the individual nucleoside units is covalently linked to at least one other nucleoside unit through a single phosphorus moiety. In the case of naturally occurring oligonucleotides, the covalent linkage in between nucleoside units is a phosphodiester bond. Oligonucleotides may be comprised of about 2 to about 100 nucleotides, more preferably from about 15 to about 60 nucleotides for clinical applications.

The term "modified oligonucleotide" as used herein includes, but is not limited to, oligonucleotides that are modified with respect to any one or more of the following: (1) the phosphodiester bond between nucleoside units, (2) the individual nucleoside units themselves and/or (3) the ribose, or sugar, moiety of the nucleoside units. Such modified oligonucleotides are best described as being functionally interchangeable with, yet structurally different from, natural oligonucleotides. Representative modifications of oligonucleotides include phosphorothioate, phosphorodithioate, methylphosphonate, H-phosphonate, triphosphate, phosphotriester or phosphoramidate internucleoside linkages in place of phosphodiester internucleoside linkages; deaza or aza purines and pyrimidines in place of natural purine and pyrimidine bases, pyrimidine bases having substituent groups at the 5 or 6 position; purine bases having altered substituent groups at the 2, 6 or 8 positions or 7 position as 7-deazapurines; sugar units containing 5, 6 and 7-membered ring structures; modifications to the 5-carbon 2-deoxyribose, or ribose including 2'-methoxy 2'-fluoro 2'-arabino, 2'-seleno and cyclic substituents.

The term "oligonucleotide functionalized fluorine containing phthalocyanine" includes, but is not limited to a fluorine containing phthalocyanine functionalized with oligonucleotides. The oligonucleotides may be substituted, e.g., with azido, amino, allyl, halogen, hydroxyl, sulfhydryl (SH), phosphoryl, alkyl and functionalized alkyl groups. These functional groups or substituents may be oriented above (beta) or below (alpha) the plane defined by the furanose ring. In some embodiments, the oligonucleotide functionalized fluorine containing phthalocyanine includes heterocyclic bases selected from the group consisting of adenine, cytosine, guanine, thymine, uracil, and other heterocycles such as inosine, 5-methylcytosine, 5-fluorocytosine, 5-bromocytosine, 5-iodocytosine, isocytosine, $N_4$-methylcytosine, 5-iodouracil, 5-fluorouracil, 4-thiouracil, 2-thiouracil, (E)-5-(2-bromovinyl)uracil, 2-thiothymine, 4-thiothymine, 7-deazaadenine, 9-deazaadenine, $N_6$-methyladenine, 2-chloroadenine, 2-fluoroadenine, 2-chloroadenine, isoguanine, 3-deazaadenine, 7-deazaguanine, 8-oxoguanine, 9-deazaguanine, 6-thioguanine, nicotinamide, 2-aminopurine, 2,6-diaminopurine, N6-cyclopropyl-2,6-diaminopurine, hypoxanthine, 6-thiohypoxanthine, and 1,2,4-triazole-3-carboxamide.

A representative example of an oligonucleotide functionalized fluorine containing phthalocyanine may be depicted as follows:

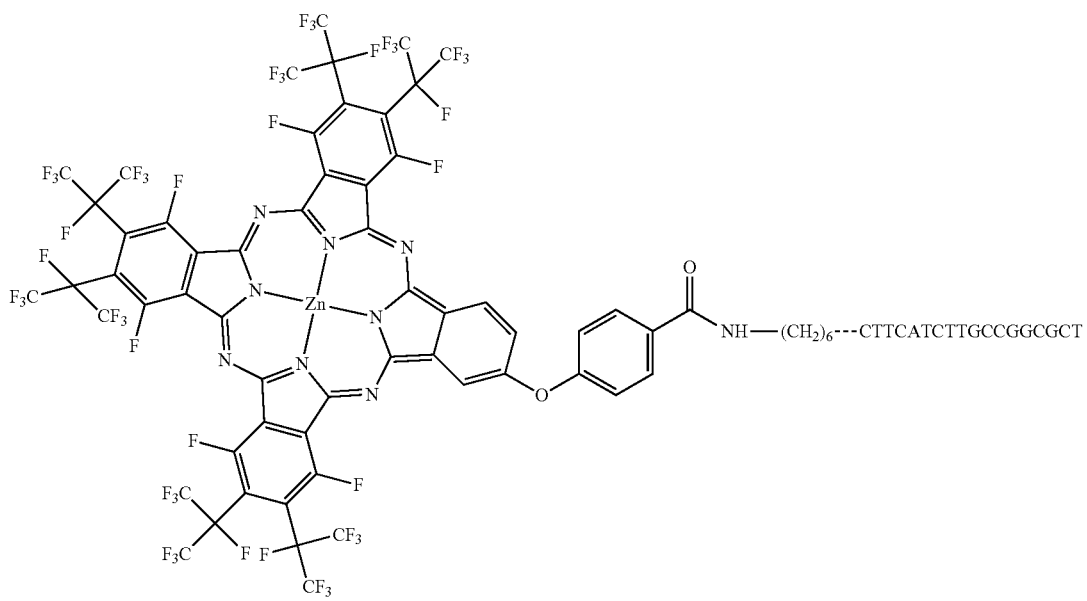

In the above example, the oligonucleotide contains 18 nucleotides (SEQ ID NO: 16) and is conjugated to the fluorine containing phthalocyanine via a hexamethylene $(CH_2)_6$, linker bonded to the amide group.

As used herein, "amino acids" are individual units containing an N-terminal amino group, a C-terminal carboxylic acid group, an alpha-carbon which projects a side-chain and a hydrogen in a tetrahedral geometry. The side-chain is any of the groups containing a hydrogen, alkyl, functionalized alkyl, cycloalkyl, heterocycloalkyl and heterobicycloalkyl which includes any of the side-chains found within the native amino acids, alanine, arginine, asparagine, aspartic acid, cysteine, glutamic acid, glycine, histidine, isoleucine, leucine, lysine, methionine, phenylalanine, proline, serine, threonine, tryptophan, tyrosine, valine, but also any modified or analogous forms thereof. Representative examples of non-naturally occurring amino acids include, D-alanine, p-aminobenzoic acid, aminobutyric acid, aminohexanoic acid, aminoisobutyric acid, D-arginine, D-asparagine, D-aspartic acid, butylglycine, citrulline, cyclohexylalanine, D-cysteine, diaminobutanoic acid, diaminopropionic acid, dihydroxyphenylalanine, D-glutamic acid, D-glycine, D-histidine, D-homoserine, D-hydroxyproline, D-isoleucine, isonipecotic acid, D-leucine, D-lysine, D-methionine, norleucine, norvaline, ornithine, D-phenylalanine, phenylglycine, D-proline, sarcosine, D-serine, statine, tetrahydroisoquinoline-3-carboxylic acid, thienylalanine, D-threonine, D-tryptophan, D-tyrosine, D-valine, α,β,γ-amino acids, lactam amino acids, and aza-amino acids.

As used herein, "peptides" are polymers of at least two amino acid units, wherein each of the individual amino acid units are covalently linked through a peptide bond. In the case of naturally occurring peptides, the covalent linkage in between amino acid units is an amide bond. Peptides may be about 2 to about 30 amino acids, and more preferably from about 5 to about 10 amino acids for clinical applications.

The term "modified peptide", as used herein, may include peptides that are modified with respect to any one or more of the following: (1) the peptide bond in between amino acid units, and/or (2) the individual amino acid units themselves. Such modified peptides are functionally interchangeable with, yet structurally different from, natural peptides. Representative modifications of peptides include cyclic peptides, bicyclic peptides, isopeptides, N-alkyl peptides, azapeptides, depsipeptides, D-peptides, peptoids, β- or γ-peptides.

A "peptide functionalized fluorine containing phthalocyanine" includes, a fluorine containing phthalocyanine functionalized with a peptide. The peptide may be substituted, e.g., azido, amino, allyl, halogen, hydroxyl, sulfhydryl (SH), phosphoryl, alkyl and functionalized alkyl groups. These functional groups or substituents may be oriented in the L-(S) or D-(R) configurations at the alpha-carbon position.

In some embodiments, the peptide functionalized fluorine containing phthalocyanine includes a heterocyclic substituent, e.g., indole, pyrrole, thienyl, oxazolinyl, imidazoyl, furyl.

A representative example of a peptide functionalized fluorine containing phthalocyanine includes

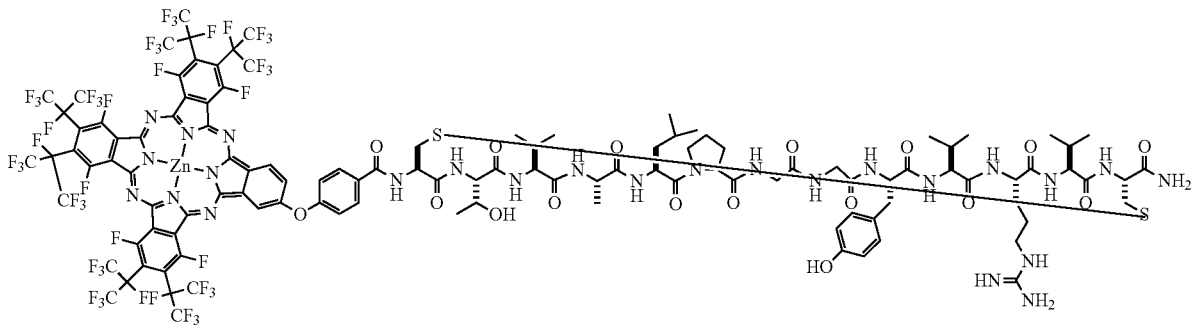

In the above example, the peptide contains 13 amino acids (SEQ ID NO: 17) and is conjugated to the fluorine containing phthalocyanine by an amide bond.

As used herein, "short-interfering RNA or siRNA", are polymers or complexes of two antiparallel complementary oligonucleotides forming double-stranded RNA. The complementary oligonucleotides may each be about 18 to about 28 nucleotides in length, wherein the double-stranded siRNA molecule has an 18-23 base-pair duplex portion, and a 1-5 nucleotide 3' overhang in each strand that may or may not be phosphorylated.

The siRNA or siRNA-like molecule has the ability to inhibit protein translation by eliciting RISC-mediated cleavage of a target mRNA strand. The siRNA molecule may contain oligonucleotides that are modified with respect to any one or more of the following: (1) the phosphodiester bond between nucleoside units, (2) the individual nucleoside units themselves (3) the ribose, or sugar, moiety of the nucleoside units, and/or (4) the global structure of the siRNA molecule [Maina, A. et. al. (2013) Solid-phase synthesis, characterization and RNAi activity of branch and hyperbranch siRNAs. Bioorg. Med. Chem. Lett. 23, 5270-5274]. Such modified oligonucleotides are best described as being functionally interchangeable with, yet structurally different from, natural oligonucleotides. Representative modifications of oligonucleotides include phosphorothioate, phosphorodithioate, methylphosphonate, H-phosphonate, triphosphate, phosphotriester or phosphoramidate internucleoside linkages in place of phosphodiester internucleoside linkages; deaza or aza purines and pyrimidines in place of natural purine and pyrimidine bases, pyrimidine bases having substituent groups at the 5 or 6 position; purine bases having altered substituent groups at the 2, 6 or 8 positions or 7 position as 7-deazapurines; sugar units containing 5, 6 and 7-membered ring structures; modifications to the 5-carbon 2-deoxyribose, or ribose including 2'-methoxy 2'-fluoro 2'-arabino, 2'-seleno and cyclic substituents. siRNA will be readily understood by persons skilled in the art as representing molecules being capable of entering the RNAi pathway to inhibit the expression of a specific gene in a sequence dependent manner.

The term "sense strand" is to be understood as the oligonucleotide strand of a double-stranded DNA or RNA oligonucleotide molecule that is generally considered to code for amino acids, and from which proteins may be translated (although regions of the sense strand may be untranslated or untranscribed). Messenger RNA (mRNA), which will be well known to persons skilled in the art, is considered to be sense strand RNA.

The term "antisense strand" is to be understood as referring to the other strand of a double-stranded DNA or RNA oligonucleotide molecule, which is not generally considered to code for amino acids or proteins (i.e., the "nonsense strand"; although there may be some rare circumstances where the antisense strand does, in fact, code for amino acids or proteins). Both of these terms will be readily understood by persons skilled in the art.

As used herein, the term "complementary" is to be understood to describe the relationship between two strands of a double-stranded DNA or RNA oligonucleotide molecule, wherein the two strands hybridize to each other via the well-known Watson-Crick base-pairing bonds, such that adenine (A) bases pair with uracil (U) bases in RNA strands or thymine (T) bases in DNA strands; and cytosine (C) bases pair with guanine (G) bases in both RNA and DNA strands.

For purposes of the present invention, the term "cancer" refers to any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Representative examples of different types of cancer include liver cancer, lung cancer, colon cancer, rectal cancer, anal cancer, bile duct cancer, small intestine cancer, stomach (gastric) cancer, esophageal cancer; gallbladder cancer, pancreatic cancer, appendix cancer, breast cancer, ovarian cancer; cervical cancer, prostate cancer, renal cancer (e.g., renal cell carcinoma), cancer of the central nervous system, glioblastoma, skin cancer, lymphomas, choriocarcinomas, head and neck cancers, osteogenic sarcomas, and blood cancers. Non-limiting examples of specific types of liver cancer include hepatocellular carcinoma (HCC), neuroblastoma, secondary liver cancer (e.g., caused by metastasis of some other non-liver cancer cell type), and hepatoblastoma. As used herein, a "tumor" comprises one or more cancerous cells.

The term "cancer gene or oncogene" refers to any member of a class of disease causing genes characterized by the uncontrolled growth of aberrant cells. The term includes all known cancer genes that are mutated and/or lead to over expression of proteins or oncoproteins that results in the formation of neoplastic conditions, whether characterized as malignant, benign, soft tissue, or solid, and cancers of all stages and grades including pre- and post-metastatic cancers. Representative examples of different types of cancer genes or oncogenes include GRP78, c-Myc, Vascular Endothelial Growth Factor (VEGF), BCL-2, Casein kinase 1α subunit, Casein kinase 2β subunit, Hypoxia inducible Factor 1a, Histone deacetylase 6, ATP-dependent DNA ligase 1 and poly-ADP ribose polymerase 1.

The term "subject" is meant as an individual, domesticated animals, such as cats, dogs, etc., livestock (e.g., cattle, horses, pigs, sheep, goats, etc.), laboratory animals (e.g., mouse, rabbit, rat, guinea pig, etc.) and birds. Preferably, the subject is a mammal such as a primate including a human.

The term "biological system" refers to referring to a "living system" or system containing biological entities. Representative examples of a biological system include mammalian or bacterial cell lines, tissues, animals as well as humans.

The term "therapeutically effective amount" means an amount sufficient to produce a desired therapeutic effect. Therefore, the amount of the CTL-functionalized fluorine containing Pc may vary depending on various factors including the kind and severity of the disease to be treated, the kind of CTL-functionalized fluorine containing Pc to be administered, the kind of the formulation to be used, the patient's age, body weight, general health, gender and diet, the time of administration, the route of administration, the duration of the treatment, and other drugs used in combination or coincidentally with the composition and like factors well known in the medical arts.

Functionalized Fluorine Containing Phthalocyanine

A functionalized fluorine containing phthalocyanine of the present application can have the formula $(R_f)_x R'_y (R)_z$ PcM The numbers x and y are integers or zero, provided that $0<x+y<16$. The number n is an integer, such that $n \geq 1$. All isomers, e.g., structural isomers, stereoisomers, mirror-image enantiomers, etc. are possible in the above mentioned formula for a functionalized fluorine containing phthalocyanine of the present application.

In some embodiments, one possible isomer of the above formula, where x+y=15 and z=1, is shown in the exemplary functionalized fluorine containing phthalocyanine may be represented by Formula (I):

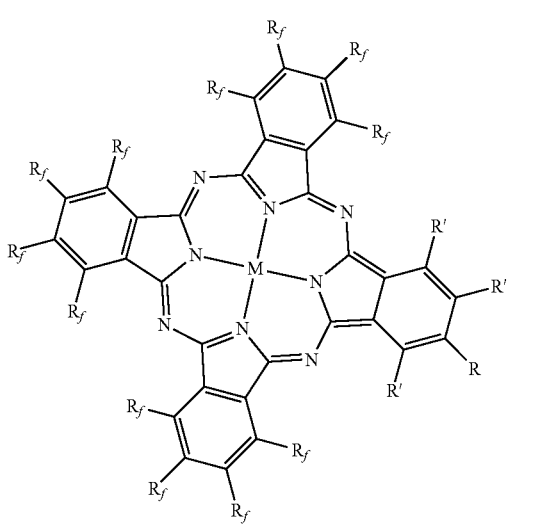

Formula (I)

$R_f$ can be selected from the group consisting of fluorine (F), a fluorocarbon containing from 1 to 18 carbon atoms, a fluorine containing group, a non-fluorine containing group, and combinations thereof. A non-fluorine containing group can include a functional group directly attached to the phthalocyanine macrocycle or metal/non-metal center. Exemplary non-fluorine containing groups may include nitro, chloro, sulfonate, thiol, hydroxo, hydrocarbon, or groups that are known in the art to act as aromatic substituents. In one embodiment, a hydrocarbon group can be attached to the aromatic ring of the phthalocyanine, and another non-fluorine containing group can be attached to the hydrocarbon. In some embodiments, at least one $R_f$ contains a fluorine atom. The inclusion of fluorine in at least one $R_f$ can provide higher thermal and chemical stability.

R' can be selected from the group consisting of fluorine (F), a fluorocarbon containing from 1 to 18 carbon atoms, a fluorine containing group, a non-fluorine containing group, and combinations thereof. In some embodiments, all R' are hydrogen atoms.

R may include at least one of a reactive functional group or at least one cancer-targeting ligand (CTL). In some embodiments, the reactive functional group or the at least one CTL can be directly attached to the phthalocyanine macrocycle. In some embodiments, intervening atoms or groups, e.g., linkers, may be used to attach the reactive functional group or the at least one CTL to the phthalocyanine. For example, as shown by the exemplary oligonucleotide and peptide functionalized fluorine containing phthalocyanine, a peptide or a nucleotide is bonded to a phthalocyanine via the formation of peptide bond. In these examples, R can include a carboxylic group and a phenoxy group as linkers to attach the nucleotide or peptide to the phthalocyanine. Exemplary linkers can include the alkyl, heteroalkyl, aryl, heteroaryl, cyclyl, bicyclyl, heterocyclyl, and the heterobicyclyl groups. It should be obvious to those skilled in the art that other intervening atoms could be used to anchor the reactive functional group or the at least one CTL to the phthalocyanine macro cycle.

M may be a metal, a non-metal, at least one of a metal or non-metal in complex or covalently bonded to at least one axial ligand.

The functionalized fluorine containing phthalocyanine may be in the form of a salt. Pharmaceutically acceptable salts refers to the relatively non-toxic, inorganic and organic acid addition salts of the Pcs. These salts can be prepared in situ during the final isolation and purification of the photosensitizer(s), or by separately reacting a purified photosensitizer(s) in its free base form with a suitable organic or inorganic acid, and isolating the formed salt. Exemplary salts include the hydrobromide, hydrochloride, sulfate, bisulfate, phosphate, nitrate, acetate, pyruvate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example, Berge et al. (1977) "Pharmaceutical Salts", J. Pharm. Sci. 66:1-19).

R can include a reactive functional group can include a carboxylic acid group, an aldehyde group, an amino group, a hydrazine group, an alkyne, alkene or a diene group an azido group, an isocyanate group, an acyl halide, a hydroxide, a thiol, a nitro, a halogen, a phosphate group, an amide or combinations thereof. The reactive functional group can serve as a point of attachment for a ligand. It will be obvious to those skilled in the art that other functional groups may also serve the same purpose.

$R_f$ can include fluoroalkyl (e.g., perfluoroalkyl), fluoroalkylcylic, fluoroalkylbicyclic, fluoroaryl, fluoroheteroaryl, fluoroheterocyclic, and fluoroheterobicyclyl. It will be obvious to those skilled in the art that other fluorocarbons having 1 to 18 carbon atoms can be used.

The alkyl group of the fluoroalkyl may be methyl, ethyl, propyl, butyl, cycloalkyl and functionalized alkyl groups. The functionalized alkyl group may be methylamino, dimethylamino, ethylamino, diethylamino, propylamino, butylamino, alkoxy, alkylsulhydryl, haloalkyl and phosphoryl groups. The alkoxy may be methoxy, levulinyl, carboxy, ethoxy, propoxy and functionalized alkoxy groups. The functionalized alkoxy group may be —O(CH$_2$)q-R, where q=2-4 and R is —NH$_2$, —OCH$_3$, or —OCH$_2$CH$_3$. The alkoxyalkyl group may be methoxyethyl, and ethoxyethyl. The haloalkyl group may be —CF$_3$, —CBr$_3$, —CCl$_3$ and —CI$_3$.

The aryl group of the fluoraryl may be phenyl, benzyl, phenol, naphthyl, bi-aryl, trityl, functionalized trityl carbobenzyloxy, functionalized carbobenzyloxy. The functionalized trityl group may be trityl-R, where R is —OC(CH$_3$)$_3$, —OCH$_3$, or —OCH$_2$CH$_3$. The functionalized carboxybenzyloxy group may be selected from the group consisting of CO-aryl-R, where R is a halogen (—Cl, —F, —Br, —I, alkyl or alkoxyalky (—OC(CH$_3$)$_3$, —OCH$_3$, or —OCH$_2$CH$_3$).

The alkylcyclic group of the fluoroalkylcyclic may be cyclopropyl, cyclobutyl, cyclopentyl and cyclohexyl.

The alkylbicyclic group of the fluoroalkylbicyclic may be di-cyclobutyl, di-cyclopentyl and di-cyclohexyl.

The heterocyclic group of the fluoroheterocyclic may be pyrimidinyl, pyrrolo, pyridinyl, oxazolinyl, aza-oxazolinyl, thio-oxazolinyl, thiophenyl, furyl, or imidazolyl.

The heterobicyclic group of the fluoroheterobicyclic may be purinyl, steroyl, indoyl and quinolyl.

M can be a metal or non-metal. The metal is not limited to a diamagnetic metal. Exemplary metals can Zn$^{2+}$, Mg$^{2+}$, low-spin Fe$^{2+}$, Ru$^{2+}$, Pt$^{2+}$, or Ti$^{4+}$. Exemplary non-metals can include Si$^{4+}$. The metal or non-metal can be in complex with, or covalently bound to at least one axial ligand. In some embodiments, the metal can be in complex with or covalently bound to up to two axial ligands. The metal can be coordinated to a phthalocyanine moiety, for example, such as depicted in Formula I.

Each axial ligand can be any atom or group of atoms, similar or different that can coordinate M. It should be understood that an axial ligand may not be present in a certain M, and that more than one axial ligand may be present in a certain M. Each axial ligand may be independently selected, and may include H, alkylamino, alkylthio, alkoxy, alkylseleno, alkylsulfonyl, $C(S)NHC_6H_{11}O_5$, $OC(O)CH_3$, $OC(O)$, CS, CO, CSe, OH, O (oxo) and an alkyl group having from 1 to 12 carbon atoms, or $(CH_2)_nN((CH)_o(CH_3))_2$, wherein n is an integer from 1 to 12; and o is an integer from 1 to 11, or a pharmaceutically acceptable salt thereof (to achieve a neutral charge).

In some embodiments, M may be represented by $(G)_aY[(OSi(CH_3)_2(CH_2)_bN_c(R')_d(R'')_e)_fX_g]_p$, wherein a is 0 or 1, b is an integer from 2 to 12, c is 0 or 1, d is an integer from 0 to 3, e is an integer from 0 to 2, f is 1 or 2, g is 0 or 1, and p is 1 or 2. Y may be selected from Si, Al, Ga, Ge, or Sn. R' may be selected from H, $CH_3$, $C_2H_5$, $C_4H_9$, $C_4H_8NH$, $C_4H_8N$, $C_4H_8NCH_3$, $C_4H_8S$, $C_4H_8O$, $C_4H_8Se$, $OC(O)CH_3$, $OC(O)$, CS, CO, CSe, OH, $C_4H_8N(CH_2)_3CH_3$, $(CH_2)_2N(CH_3)_2$, an alkyl group having from 1 to 12 carbon atoms, and $(CH_2)_nN((CH_2)_o(CH_3))_2$, wherein n is an integer from 1 to 12; and o is an integer from 1 to 11. R'' may be selected from H, $SO_2CH_3$, $(CH_2)_2N(CH_3)_2$, $(CH_2)_{11}CH_3$, $C(S)NHC_6H_{11}O_5$, an alkyl group having from 1 to 12 carbon atoms, and $(CH_2)_nN((CH_2)_o(CH_3))_2$, wherein n is an integer from 1 to 12; and o is an integer from 1 to 11. G may be selected from OH and $CH_3$. X may be selected from I, F, Cl, or Br.

M may include at least one metal, at least one non-metal, or a combination of a metal and a non-metal. Exemplary M include $AlOSi(CH_3)_2(CH_2)_3N(CH_3)_2$, $AlOSi(CH_3)_2(CH_2)_3N(CH_3)_3^+I^-$, $CH_3SiOSi(CH_3)_2(CH_2)_3N(CH_3)_2$, $HOSiOSi(CH_3)_2(CH_2)_3N(CH_3)_2$, $HOSiOSi(CH_3)_2(CH_2)_3N(CH_3)_3^+I^-$, $Si[OSi(CH_3)_2(CH_2)_3N(CH_3)_3^+I^-]_2$, $Si[OSi(CH_3)_2(CH_2)_4NH_2]_2$, $Si[OSi(CH_3)_2(CH_2)_4NHSO_2CH_3]_2$, $HOSiOSi(CH_3)_2(CH_2)_4NHSO_2CH_3$, $HOSiOSi(CH_3)_2(CH_2)_3N(CH_2CH_3)(CH_2)_2N(CH_3)_2$, $Si[OSi(CH_3)_2(CH_2)_4NHCSNHC_6H_{11}O_5]_2$, $Si[OSi(CH_3)_2(CH_2)_3N(CH_3)_2]_2$, $HOSiOSi(CH_3)_2(CH_2)_3OCOCH_3$, $HOSiOSi(CH_3)_2(CH_2)_3OH$, $Si[OSi(CH_3)_2(CH_2)_3N(CH_2CH_3)(CH_2)_2N(CH_3)_2]_2$, $HOSiOSi(CH_3)_2(CH_2)_3NC_4H_8O$, $AlOSi(CH_3)_2(CH_2)_3N^+(CH_3)_2(CH_2)_{11}CH_3I^-$, $HOSiOSi(CH_3)_2(CH_2)_8N(CH_3)_2$, $Si[OSi(CH_3)_2(CH_2)_3NC_4H_8O]_2$, $HOSiOSi(CH_3)_2(CH_2)_3NC_4H_8S$, $HOSiOSi(CH_3)_2(CH_2)_3N(CH_2)_3(CH_3)_2$, $HOSiOSi(CH_3)_2(CH_2)_3NCS$, $HOSiOSi(CH_3)_2(CH_2)_3N[(CH_2)_3N(CH_3)_2]_2$, $HOSiOSi(CH_3)_2(CH_2)_3NC_4H_8NCH_3$, $Si[OSi(CH_3)_2(CH_2)_3NC_4H_8NCH_3]_2$, $HOSiOSi(CH_3)_2(CH_2)_3NC_4H_8N(CH_2)_3CH_3$, $Si[OSi(CH_3)_2(CH_2)_3NC_4H_8NH]_2$, or pharmaceutically acceptable salts thereof.

M can include $HOSiOSi(CH_3)_2(CH_2)_3N(CH_3)_2$, $HOSiOSi(CH_3)_2(CH_2)_3N(CH_2CH_3)(CH_2)_2N(CH_3)_2$, $HOSiOSi(CH_3)_2(CH_2)_3NC_4H_8O$, $HOSiOSi(CH_3)_2(CH_2)_8N(CH_3)_2$, or pharmaceutically acceptable salts thereof. In one embodiment, M is $HOSiOSi(CH_3)_2(CH_2)_3N(CH_3)_2$ or a pharmaceutically acceptable salt thereof.

M can be two protons, e.g. $H^+$.

Additional groups, such as anionic groups, may be linked to M to ensure electrical neutrality. Exemplary anionic groups can include halogens or oxo groups. For example, if M is $Si^{4+}$, two $Cl^-$ bonded to the Si, or an oxo group, or two hydroxyl groups ensures electrical neutrality.

The cancer-targeting ligand (CTL) can include cancer-targeting small molecules (e.g. folate), cancer-targeting peptides (e.g., Pep42, RGD (SEQ ID NO: 37)), cancer-targeting proteins (e.g., antibodies such as monoclonal antibodies and fragments thereof that bind to proteinaceous receptors on cancer cells), cancer-targeting lipids (e.g., palmitic acid), cancer-targeting carbohydrates and glycoconjugates (e.g., sialic acid, cancer-targeting nucleosides, nucleotides and oligonucleotides (e.g., aminoacylnucleolipids, antisense, siRNA, miRNA, ribozymes, aptamers).

The literature describes many cancer-targeting oligonucleotides, CTOs, and cancer-targeting peptides, CTPs, that may be used with the functionalized fluorine containing phthalocyanine molecules of the present application. See, e.g., United States Patent Application Publication (USAP) 20130065939 (siRNA molecules which silence the expression of at least 1, 2, 3, 4, 5, 6, 7, or all 8 of the following genes: COP1, WEE1, HDAC2, RBX1, CDK4, CSN5, FOXM1, and R1 (RAM2)); USAP 20130039971 (an isolated siRNA which targets human VEGF mRNA, or an alternative splice form, mutant or cognate thereof); USAP 20130023578 (siRNA molecules that complementary binds to a base sequence of c-Met transcript (mRNA transcript), thereby inhibiting expression of c-Met without eliciting immune responses, and use of the siRNA for prevention and/or treatment of cancer); USAP 20130028957 (siRNA molecule for inhibiting expression of the FLJ25416 gene expressed in cancer cells); USAP 20120308645 (siRNA-mediated down-regulation of HIF-1 alpha that can be used to inhibit angiogenesis, diabetic retinopathy, age related macular degeneration and many types of cancer); USAP 20120252011 (siRNA that inhibits expression of at least one gene selected from the group consisting of SON gene, MCM5 gene, WDR5 gene, PBK gene and CENPA gene); USAP 20120071540 (use siRNA molecules for the treatment of breast cancer); USAP 20110245325 (siRNA molecule that directs cleavage of mRNA of mucin subtype 5 AC via RNA interference); USAP 20100239596 (use of siRNA molecule to inhibit the expression of GRP78 protein; USAP 20110207798 (adenine nucleotide translocator 2 (ANT2) siRNA (small interfering RNA) or ANT2 shRNA (short hairpin RNA) suppressing the expression of ANT2 gene in breast cancer); USAP 20110190384 (a growth suppression of solid tumor, and to an induction of cell death in the solid tumor, by means of siRNA that suppresses an expression of WT117AA(−) isoform); USAP 20110142915 (siRNA compositions and methods useful for inhibiting expression of vascular endothelial growth factor (VEGF) isoforms); USAP 20110129461 (siRNA or shRNA molecules directed to MAT II .beta. subunit to inhibit its expression for the treatment of leukemia); USAP 20110039915 (siRNA molecule that is capable of silencing gene expression as well as inducing an immune response; USAP 20100286244 (use of siRNA molecule to inhibit Nuclear Mitotic Apparatus Protein (NuMA) gene expression); USAP 20100317840 (siRNA sequence partially or completely complementary to the sequence of hnRNP K is used to inhibit hnRNP K expression); USAP 20100285107 (use of short nucleic acid molecules that modulate Aurora-B kinase (AurkB) expression); USAP 20100173976 (use of siRNA molecules for inhibition of stromal cell-derived factor-1 (SDF-1) gene expression); USAP 20100172962 (siRNA is targeted to a nucleic acid encoding an interleukin); USAP 20100093835 (siRNA molecules used to modulate the expression of Myc and/or Myb (e.g., c-Myc, N-Myc, L-Myc, c-Myb, a-Myb, b Myb, and v-Myb) genes); USAP 20090311716 (use of siRNA specific for protocadherin-PC, or other inhibitors of protocadherin-PC expression or activity for the treatment and prevention of hormone-resistant prostate cancer).

The oligonucleotides can have a length of about 2 to about 100 nucleotides. Among other applications, the oligonucleotides are capable of targeting oncogenes leading to gene silencing in cancer as discussed herein.

The oligonucleotide can be coupled to a phthalocyanine, such as that of Formula I, by a reactive functional group. The reactive functional group includes a carboxylic acid group, an aldehyde group, an amino group, a hydrazine group, an alkyne, alkene or a diene group an azido group, an isocyanate group, an acyl halide, a hydroxide, a thiol, a nitro, a halogen, a phosphate group, an amide or combinations thereof.

The oligonucleotide may include nucleotides or modified nucleotides such as deoxyadenylate, deoxyguanylate, deoxythymidylate, deoxycytidylate, adenylate, guanylate, uridylate, cytidylate, 2'-methoxynucleotides, 2'-fluoronucleotides, 2'-arabinonucleotides, 2'-selenonucleotides and locked nucleotides.

The oligonucleotide can include at least one of a first oligonucleotide and a second oligonucleotide, where the second oligonucleotide, when present, may be complementary or non-complementary with the first oligonucleotide. In some embodiments, the oligonucleotide may be hybridized to a complementary oligonucleotide forming an siRNA-like molecule. In some embodiments, the siRNA-like molecule can be double-stranded. In some embodiments, the siRNA-like molecule can be single stranded. The siRNA-like molecules can include at least one of a first oligonucleotide and a second oligonucleotide. The first and second oligonucleotides may be about 18 to about 28 nucleotides in length. In another embodiment, the double-stranded siRNA or siRNA-like molecule comprises a 18-23 bp duplex portion. The siRNA-like molecule can trigger oncogene silencing effects in cancer cells leading to arrest of oncoprotein production and ultimately leading to cancer cell death. In some embodiments, when the second oligonucleotide is present, one or both oligonucleotide strands have overhangs from about 1 to about 5 nucleotides on the 3'-end. In some embodiments, neither strand has an overhang. In some embodiments, one or both oligonucleotide strands comprise chemical modification(s) at one or more terminal nucleotides to confer resistance to nuclease degradation.

The oligonucleotide may be capped. In some embodiments, the oligonucleotide is capped with modified nucleotides or moieties that confer exonuclease resistance. Various modified nucleotides or moieties having similar properties may be used. Exemplary modified nucleotides or moieties include 2'-methoxynucleotides, 2'-fluoronucleotides, 2'-arabinonucleotides, 2'-selenonucleotides and locked nucleotides. In some embodiments, the ends of the oligonucleotides are capped with modified nucleotides or moieties capable of cell signaling or detection. Exemplary modified nucleotides or moieties include phthalocyanines, fluorescein, 5-tetrachlorofluorescein, 5-hexachlorofluorescein, rhodamine, dabcyl, biotin, cyanine, dylight, epoch, black hole quenchers, acridine, pyrene, nitrophenyl, 2,4-dinitrophenyl, cholesterol, tocopherol, stearyl, EDTA, ferrocene, isotopic labels, radionuclides and spin labels.

The CTL may be a peptide. The peptide may be about 2 to about 30 amino acids in length. The peptide can target oncoprotein receptors located on the surface of cancer cells.

The peptide can be coupled to a phthalocyanine, such as shown in Formula I, by a linkage. Exemplary linkages can include one or more of amide, urea, thiourea, carbonate, carbamate, hydrazino, diacylhydrazine, semicarbazido, N-alkyl, N-phosphoryl, N-sulfuryl and any combination thereof.

The peptide can include amino acids or modified amino acids selected from the group consisting of alanine, p-aminobenzoic acid, aminobutyric acid, aminohexanoic acid, aminoisobutyric acid, arginine, asparagine, aspartic acid, butylglycine, citrulline, cyclohexylalanine, cysteine, diaminobutanoic acid, diaminopropionic acid, dihydroxyphenylalanine, glutamic acid, glycine, histidine, homoserine, hydroxyproline, isoleucine, isopipecotic acid, leucine, lysine, methionine, norleucine, norvaline, ornithine, phenylalanine, phenylglycine, proline, sarcosine, serine, statine, tetrahydroisoquinoline-3-carboxylic acid, thienylalanine, threonine, tryptophan, tyrosine, and valine.

The peptides can include chemical modification(s) at one or more amino acids. In some embodiments, the chemical modification(s) may confer resistance to degradation. Exemplary modified amino acids or moieties include D-alanine, p-aminobenzoic acid, aminobutyric acid, aminohexanoic acid, aminoisobutyric acid, D-arginine, D-asparagine, D-aspartic acid, butylglycine, citrulline, cyclohexylalanine, D-cysteine, diaminobutanoic acid, diaminopropionic acid, dihydroxyphenylalanine, D-glutamic acid, D-glycine, D-histidine, D-homoserine, D-hydroxyproline, D-isoleucine, isopipecotic acid, D-leucine, D-lysine, D-methionine, norleucine, norvaline, ornithine, D-phenylalanine, phenylglycine, D-proline, sarcosine, D-serine, statine, tetrahydroisoquinoline-3-carboxylic acid, thienylalanine, D-threonine, D-tryptophan, D-tyrosine, D-valine, lactam amino acids, and aza-amino acids.

In some embodiments, the ends of the peptide are capped with modified moieties capable of cell signaling or detection. Representative examples of modified moieties include phthalocyanines, fluorescein, 5-tetrachlorofluorescein, 5-hexachlorofluorescein, rhodamine, dabcyl, biotin, cyanine, dylight, epoch, black hole quenchers, acridine, pyrene, nitrophenyl, 2,4-dinitrophenyl, cholesterol, tocopherol, stearyl, EDTA, ferrocene, isotopic labels, radionuclides and spin labels.

Methods of Making

Methods of making CTL-functionalized fluorine containing phthalocyanine molecules can include initially synthesizing a functionalized fluorine containing phthalocyanine having a reactive group, such as by a reaction demonstrated in FIG. 1a, and discussed in Example 1 herein. The functionalized fluorine containing phthalocyanine having a reactive group can be synthesized using microwave irradiation in yields of about 20% following silica gel chromatographic purification. The functionalized fluorine containing phthalocyanine molecule having the reactive group can be further reacted with a CTL, such as a CTP (FIG. 2A) or a CTO (FIG. 3A). 1H-Benzotriazolium 1-[bis(dimethylamino)methylene] 5chloro-,hexafluorophosphate (1-),3-oxide, HCTU, coupling conditions can be optimized to couple the functionalized fluorine containing phthalocyanine molecule to a CTP (FIG. 2A) or a CTO (FIG. 3A). The CTO- or CTP-functionalized fluorine containing phthalocyanine molecules can be isolated in purities >95%. In some embodiments, the molecules can be isolated using high pressure liquid chromatography (HPLC). Their identities can be confirmed by mass spectrometry (FIGS. 2B and 3B), or other suitable analytical techniques.

Pharmaceutical Composition

The functionalized fluorine containing pthyalocyanine molecules may be used to treat diseases, including but not limited to, cancer, angiogenic-related diseases, infectious diseases, neurodegenerative disorders, genetic, metabolic and protein mis-folded diseases.

The functionalized fluorine containing phthalocyanine molecules may be formulated with a pharmaceutically acceptable carrier to form a pharmaceutical composition for administration to a subject in accordance with known techniques and acceptable medical practice. "Pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. The carrier is "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Representative examples of a pharmaceutically acceptable carrier include cationic lipids, cationic amphiphilic polymers, aminoacyl nucleolipids, membrane-permeable peptides, cancer-targeting peptides, ferritins, lipids and steroids.

The pharmaceutical composition can be administered by numerous methods as discussed herein. For example, in some embodiments, the pharmaceutical composition can be administered systemically (e.g, parenterally).

By way of examples, topical administration of the pharmaceutical composition may be accomplished using, powders, sprays, ointments, pastes, creams, lotions, gels, solutions, or patches. The active component, e.g., a functionalized fluorine containing phthalocyanine, may be mixed under sterile conditions with a pharmaceutically acceptable carrier, and, optionally, with any one or combination of preservatives, buffers, or propellants which may be required. The ointments, pastes, creams, solutions, foams, lacquers, oils and gels may contain excipients in addition to functionalized fluorine containing phthalocyanine. These formulations may contain a functionalized fluorine containing phthalocyanine within or on micro or nanoparticles, liposomes, beads, polymer matrices, sponges, osmotic pumps, or other structures.

Powders and sprays can contain, in addition to a functionalized fluorine containing phthalocyanines, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane. In certain embodiments, a composition comprising a compound of any one of formulae I-IV may be prepared according to U.S. Pat. No. 6,617,356, U.S. Pat. No. 5,914,334, or U.S. Pat. No. 6,617,356.

The pharmaceutical composition can be alternatively administered by aerosol. This can be accomplished by preparing an aqueous aerosol, liposomal preparation, or solid particles containing the compound. A non-aqueous (e.g., fluorocarbon propellant) suspension could be used. Sonic nebulizers are preferred because they minimize exposing the agent to shear, which can result in degradation of the compound. Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

Transdermal patches have been reported to possess the added advantage of providing controlled delivery of a functionalized fluorine containing phthalocyanine to the body. Such dosage forms can be made by dissolving or dispersing the functionalized fluorine containing phthalocyanine in the proper medium. Absorption enhancers can also be used to increase the flux of the photosensitizer(s) into the skin. The rate of such flux can be controlled by either providing a rate controlling membrane or dispersing the phthalocyanine in a polymer matrix or gel.

Delivery of functionalized fluorine containing phthalocyanine across an epithelial, epidermal, serosal or mucosal surface may be accomplished using application of an electrical current and a charged solvent solution, such as iontophoresis.

One skilled in the art can readily determine an therapeutically effective amount of the functionalized fluorine containing phthalocyanine to be administered to a given subject, by taking into account factors such as the size and weight of the subject; the extent of the neovascularization or disease penetration; the age, health and sex of the subject; the route of administration; and whether the administration is regional or systemic. Generally, an effective amount of the functionalized fluorine containing phthalocyanine comprise an intracellular concentration at or near the neovascularization site of from about 1 nanomolar (nM) to about 100 nM, preferably from about 2 nM to about 50 nM, more preferably from about 2.5 nM to about 10 nM. In some embodiments, the peptide-functionalized fluorine containing phthalocyanine can be administered in nanomolar concentrations and the oligonucleotide-functionalized fluorine containing phthalocyanine can be administered in picomolar concentrations.

The pharmaceutical composition can be applied to an organ or tissue as a step in photodynamic therapy. In certain embodiments, the composition is applied to an epithelial, mesothelial, synovial, fascial, or serosal surface, including, but not limited to, the eye, esophagus, mucous membrane, bladder, joint, tendon, ligament, bursa, gastrointestinal, genitourinary, pleural, pericardial, pulmonary, or uroepithelial surfaces. In certain embodiments, the composition is applied to the surface of the skin.

The pharmaceutical composition may be administered alone (monotherapy), or in combination with one or more therapeutically effective anti-cancer agents or treatments (combination therapy) and/or therapeutically active agents. The other therapeutically effective agent may be conjugated to the functionalized fluorine containing-Pc, incorporated into the same composition as the functionalized fluorine containing-Pc, or may be administered as a separate composition. The other therapeutic agent or treatment may be administered prior to, during and/or after the administration of the functionalized fluorine containing-Pc. The other therapeutically effective agent may administered to augment the therapeutic effect of the functionalized fluorine containing-Pc, or to diminish the negative side effects of the functionalized fluorine containing-Pc of the present invention. For example, the functionalized fluorine containing-Pc can be administered in combination with therapeutic methods currently employed for treating cancer or preventing tumor metastasis (e.g., radiation therapy, chemotherapy, and surgery). For treating tumors, the functionalized fluorine containing-Pc is preferably administered to a subject in combination with radiation therapy, or in combination with chemotherapeutic agents such as cisplatin, carboplatin, cyclophosphamide, 5-fluorouracil, adriamycin, daunorubicin or tamoxifen.

Other anti-cancer therapeutically effective agents/treatments include surgery, anti-neoplastics (including chemotherapeutic agents and radiation), other OFA/iLRP antagonists, anti-angiogenesis agents, antibodies to other targets, small molecules, photodynamic therapy, immunotherapy, cytotoxic agents, cytokines, chemokines, growth inhibitory agents, anti-hormonal agents, kinase inhibitors, cardioprotectants, immunostimulatory agents, immunosuppressive agents, agents that promote proliferation of hematological cells, and protein tyrosine kinase (PTK) inhibitors.

Anti-neoplastic agents can be grouped into a variety of classes including, for example, mitotic inhibitors, alkylating agents, anti-metabolites, intercalating antibiotics, growth factor inhibitors, cell cycle inhibitors, enzymes, topoisomerase inhibitors, anti survival agents, biological response modifiers, anti-hormones, and anti-angiogenesis agents.

Diagnostic Applications

Diagnostic Applications disclosed herein can be used in vivo or in vitro. In vitro use may include any tests performed outside of a living organism, such as in cells and tissue cultures. For example, in one embodiment, an in vitro diagnostic application can be performed by spectrofluorimetry, flow cytometry and fluorescence microscopy.

In vivo use may include detection of a disease state, diagnosis of subjects, and treatment of disease. For example, in one embodiment, an in vivo diagnostic application can be performed by in vivo fluoresecence imaging.

Diagnostic applications include selectively targeting and identifying a target, such as an unhealthy or abnormal cell. The unhealthy or abnormal cell may include an element that distinguishes it from a healthy cell, such as a cell receptor, membrane spanning biologicals, such lipids, oligosaccharides, glycolipids, glycoproteins, and the like. The targeting ligand of the functionalized fluorine containing phthalocyanine molecules can have a sequence capable of binding to this element of the abnormal cell. The binding to the element of the abnormal cell can be more efficient than that to a healthy cell. In some embodiments, the binding efficiency to the abnormal cell can range from about 1 nanomolar (nM) to about 1000 nM. Binding efficiency can advantageously reduce the needed dosage of the functionalized fluorine containing phthalocyanine molecules. For example, in some embodiments, CTP-functionalized fluorine containing phthalocyanine molecules can bind to a receptor of a cancer cell. This receptor is absent in a healthy cell.

Fluorine containing phthalocyanine molecules demonstrate fluorescence capabilities making them applicable in diagnostic applications. These fluorescent fluorine containing phthalocyanine molecules can have therapeutic and diagnostic (theranostic) utility [Lau, J. T. F et al. (2014) A dual activatable photosensitizer toward targeted photodynamic therapy, J. Med. Chem. 57, 4088-4097]. In some embodiments, fluorine containing phthalocyanine molecules demonstrating fluorescence may also demonstrate the capability of forming a reactive oxygen species (ROS). Formation of ROS is discussed herein in regards to methods than can contribute to unhealthy cell death. However, the diagnostic methods disclosed herein can be used in combination with treatment methods disclosed herein.

Upon binding of the functionalized fluorine containing phthalocyanine molecule to the target of the unhealthy cell, the molecule can be illuminated with electromagnetic radiation having a wavelength ranging from about 600 nm to about 1000 nm. This wavelength range is optimum for maximum and benign tissue penetration. Thus, it can be advantageous for in vivo applications. In response to illumination, the molecule emits electromagnetic radiation ranging from about 400 to about 800 nm. This wavelength range, similar to the exciting wavelength range, allows for maximum benign tissue penetration. Thus, the emission is minimally attenuated by the tissue present in between the detector and the point of emission.

Treatment Applications

The treatment applications disclosed herein can include, but are not limited to, gene silencing or other mechanisms that can contribute to unhealthy cell death. For example, mechanisms may include using a fluorine containing phthalocyanine to catalyze the formation of ROS, where ROS can contribute to the death of an unhealthy cell, for example, by oxidation of one or more elements of the unhealthy cell, such as the cell proteins, DNA and/or RNA within the cell. For example, ROS may derivatize cellular components and deactivate them or the phthalocyanine itself, upon reduction by cellular components may inject electrons into various unhealthy cell components disrupting their normal function.

Treatment applications disclosed herein can be used in vivo or in vitro. In vitro use may include may include any tests performed outside of a living organism, such as in cells and tissue cultures For example, in one embodiment, an in vitro treatment application can be performed by spectrofluorimetry, flow cytometry and fluorescence microscopy.

In vivo use may include detection of a disease state, diagnosis of subjects, and treatment of disease. For example, in one embodiment, an in vivo treatment application can be performed by in vivo fluorescence imaging.

Similar to the diagnostic applications described herein, treatment methods include selectively targeting and identifying a target, such as an unhealthy or abnormal cell. The unhealthy or abnormal cell may include an element that distinguishes it from a healthy cell, such as a cell receptor, a DNA sequence, an RNA sequence, and membrane spanning biologicals, such lipids, oligosaccharides, glycolipids, glycoproteins, and the like. The targeting ligand of the functionalized fluorine containing phthalocyanine molecules can have a sequence capable of selectively binding to this element of the abnormal cell. For example, in some embodiments, CTP-functionalized fluorine containing phthalocyanine can bind to a receptor of a cancer cell. This receptor is absent in a healthy cell. Upon binding to the receptor of the unhealthy cell, in some embodiments, the fluorine containing phthalocyanine molecule can be illuminated to form ROS as discussed herein. The ROS can contribute to unhealthy cell death by any of the following suitable mechanism, such as redox chemistry, cellular components oxygenation, ROS attachment to cellular components, and/or extraction of cellular atoms, for example, H atoms of a cellular membrane by hydroxyl radicals.

In some embodiments, the functionalized fluorine containing phthalocyanine can be designed to inhibit the regular function or destroy an unhealthy cell after internalization through the cell membrane. In some embodiments, functionalized fluorine containing phthalocyanines can inhibit function of the unhealthy cell by hybridizing the CTL to an element of a cell, such as a gene, or other element, to inhibit its function. For example, the CTO of a CTO-functionalized fluorine containing phthalocyanine molecule can bind to an internal element within a cancer cell, such as a DNA and/or RNA sequence to inhibit function of the sequence in expression of a protein, cell reproduction, or the like. In some embodiments, the DNA and/or RNA sequence may be part of an oncogene. Simply by binding to the element, the functionalized fluorine containing phthalocyanine molecule can disrupt the function of the unhealthy cell. Optionally, in combination with disrupting the function of an unhealthy cell, the fluorine containing phthalocyanine molecule can further be illuminated to form ROS as discussed herein to contribute to death of the unhealthy cell.

In one embodiment, treatment methods are provided for cancers characterized by the over-expression of the glucose regulating protein of 78 kilodaltons (GRP78). In cancer, GRP78 over-expression generates cell surface GRP78 which signals the un-folded protein response leading to the rapid repair of cancer cell proteins, cell proliferation and arrest of cancer cell apoptosis [(a) Pfaffenbach, K. T. et al. (2011) The critical role of GRP78 in physiologic and pathologic stress, Curr. Opin. Cell Biol. 23, 150-156, (b) Ni, M. et al. (2011) Beyond the endoplasmic reticulum: atypical GRP78 in cell viability, signaling and therapeutic targeting, Biochem. J. 434, 181 188]. This receptor is absent or minimally expressed on the surface of healthy cells. Thus, targeting and deactivating cancer cell GRP78 may function as an ideal method for selectively inducing cancer cell death.

Accordingly, in some embodiments, the CTP is Pep42. The CTP, Pep42, has been used to specifically deliver chemotherapeutic agents to GRP78 over-expressing cancer cells; a bio-marker for cancer targeting applications [(a) Joseph, S. et al. (2014) Synthesis, Characterization and Biological Activity of Poly(arginine) derived Cancer-Targeting Peptides in HepG2 Liver Cancer Cells, J Pep Sci. 20, 736-745, (b) Liu, Y. et al. (2007) Mechanistic studies of a peptidic GRP78 ligand for cancer cell-specific drug delivery, Mol Pharm. 4, 435-447, (c) Kim, Y. et al. (2006) Targeting the Heat Shock Proteins on Cancer Cells: selection, characterization and cell-penetrating properties of a peptidic GRP78 ligand, Biochemistry 45, 9434-9444]. In some embodiments, the CTO is an antisense oligonucleotide which contains sequence specificity for down-regulating the GRP78 oncogene promoter sequence in tumor cells [(a) Ting, J. et al. (1988) Human gene encoding the 78,000-dalton glucose-regulated protein and its pseudogene: structure, conservation, and regulation, DNA 7, 275-286, (b) Wey, S. et al. (2012) Inducible knockout of GRP78/BiP in the hematopoietic system suppresses Pten-null leukemogenesis and AKT oncogenic signaling, Blood 119, 817-825, (c) Patel, P. et al. (2014) Chemically Robust Fluoroalkyl Phthalocyanine-Oligonucleotide Bioconjugates and their GRP78 Oncogene Photocleavage Activity Chem Commun. 50, 6309-6311]. Many other cancer-targeting ligands that can be directly coupled to a photosensitizer have been reported in the literature for potential applications in cancer-targeted PDT [St Denis T. G. et al. (2013) Synthesis, bioanalysis and biodistribution of photosensitizer conjugates for photodynamic therapy, Bioanalysis 9, 1099-1114].

In some embodiments, the treatment methods of the present invention can inhibit the over-expression of the GRP78 gene and also catalyze the formation of ROS to fragment, inhibit, and/or destroy the GRP78 gene.

Other GRP78 targeting oligonucleotide sequences are disclosed on GenBank (http://www.ncbi.nlm.nih.gov/genbank/) and are suitable for use with the present invention. These sequences and others are herein incorporated by reference in their entries as well as for individual subsequences contained therein [(a) USAP 201002395596 (GRP78 and tumor angiogenesis, (b) USAP 20110008882 Specific GRP78 expression-inhibition RNAi sequence, medicines thereof, and method thereof, (c) Chang, Y. J. et al. (2012) GRP78 knockdown enhances apoptosis via the down-regulation of oxidative stress and Akt pathway after epirubicin treatment in colon cancer DLD-1 cells, PLoS One, 7, e35123, (d) Zhang, L. H. et al. (2011) Association of elevated GRP78 expression with increased astrocytoma malignancy via Akt and ERK pathways, Brain Res., 1371, 23-31, (e) Tanimoto, R. et al. (2010) Down-regulation of BiP/GRP78 sensitizes resistant prostate cancer cells to gene-therapeutic over-expression of REIC/Dkk-3, Int. J. Cancer., 126, 1562-1569, (f) Alhoot, M. E. at al. (2012) RNA interference mediated inhibition of dengue virus multiplication and entry in HepG2 cells, PLoS One, 7, e34060). Table 1 provides GRP78 targeting sequences and their corresponding cell lines which can be used to synthesize the CTOs according to the present invention.

TABLE 1

GRP78 targeting oligonucleotide sequences and their corresponding cancer cell lines.

| SEQ ID NO | Oligonucleotides | Cell Line |
|---|---|---|
| 1 | 5'-AAGGAUGGUUAAUGAUGCUGAGAA-3' | Nasopharyngeal |
| 2 | 3'-UUCCUACCAAUUACUACGACUCUU-5' | |
| 3 | 5'-GGAGCGCAUUGAUACUAGATT-3' | Brain |
| 4 | 3'-TTCCUCGCGUAACUAUGAUCU-5' | Heart, Kidney, |
| 5 | 5'-AAGAAAAGCUGGGAGGUAAAC-3' | Pancreas |
| 6 | 3'-UUCUUUUCGACCCUCCAUUUG-5' | Colon |
| 7 | 5'-AAGAAAAGCUGGGAGGUAAAC-3' | |
| 8 | 3'-UUCCAAUGGGUACGUCAACAA-5' | Brain, Glioma |
| 9 | 5'-GGAGCGCAUUGAUACUAGATT-3' | Astrocytoma |
| 10 | 3'-TTCCUCGCGUAACUAUGAUCU-5' | |
| 11 | 5'-CGAGUGACAGCUGAAGACAAGGGUA-3' | Prostate |
| 12 | 3'-GCUCACUGUCGACUUCUGUUCCCAU-5' | Cervical |
| 13 | 5'-AGUGUUGGAAGAUUCUGAU-3' | Pancreatic |
| 14 | 3'-UCACAACCUUCUAAGACUA-5' | |
| 15 | 5'-GGAGCGCAUUGAUACUAGA-3' | Melanoma |
| 16 | 5'-CTTCATCTTGCCGGCGCT-3' | |

GRP78 targeting sequences are based on the GRP78 mRNA gene (Genbank Gene ID No. 100135840) depicted as SEQ ID NOS:1-16.

TABLE 2

Cancer targeting peptide sequences and their corresponding cancer cell lines.

| SEQ ID NO. | Peptide | Cell Line |
|---|---|---|
| 17 | CTVALPGGYVRVC | Liver, Melanoma, Neuroblastoma, Tumor lymphatics, human vasculature, lung, breast, colon, prostate pancreas, bladder |
| 18 | ASSLNIA | muscle |
| 19 | QPFMQCLCIYDASC | lung |
| 20 | XLWLLXXG | sperm |
| 21 | SFTYWTN | microglia |
| 22 | CKSTHDRLC | synovium |
| 23 | I/LGSGL | urothelium |
| 24 | CVSNPRWKC | pancreatic islets |
| 25 | WLSEAGPVVTVRALRGTGSW | cardiomyocytes |
| 26 | CGLIIQKNEC | plasma |
| 27 | PRP | breast |
| 28 | RGDLATLRQLAQEDGVVGVR | lung |
| 29 | CXNXDXRX/RC | bladder |
| 30 | CGKRK | squamous |
| 31 | HTFEPGV | medullary thyroid |
| 32 | VPWMEPAYQRFL | neuroblastoma |
| 33 | VHLGYAT | colon |
| 34 | TACHQHVRMVRP | hepatocellular |
| 35 | LVRSTGQFV | Chronic lymphocytic lymphoma |
| 36 | TSPLNIHNGQKL | head & neck |
| 37 | RGD | human vasculature |
| 38 | CGNKRTRGC | tumor lymphatics |
| 39 | RWID | murine lymphoma |
| 40 | c-Nle-D-Chg-NDFc | ovarian adenocarcinoma |
| 41 | fypLDFf | B-cell lymphoma |

The following examples are illustrative of various aspects of the invention, and do not limit the broad aspects of the invention as disclosed herein.

Example 1

The Synthesis of a Functionalized Fluorine Containing Phthalocyanine Having a Reactive Functional Group As depicted in FIG. 1A, the combination of a fluorinated phthalonitrile with a phthalonitrile bearing a carboxylic acid group (—COOH) resulted in the formation of a fluorine containing phthalocyanine molecule having a carboxylic acid group, e.g., a reactive functional group. The phthalocyanine was made by mixing a 1:1 ratio of the two phthalonitriles and 0.5 equivalents of zinc acetate in nitrobenzene (1 mL) and heating the combination to 190° C. for 20 min in a microwave reactor. Following solvent removal in vacuo, the resulting crude mixture was subjected to chromatographic purification on silica gel using hexanes/toluene, followed by acetonitrile spiked with 0.1% trifluoroacetic acid (TFA) to purify the desired product, obtained in about 20% yield.

Following chromatographic purification the molecule was isolated and characterized by NMR, UV-Vis spectroscopy and via mass spectrometry. FIG. 1B depicts a $^{19}$F NMR spectrum of the molecule. The peaks in the NMR spectrum confirms the presence of the fluorine atoms found within the phthalocyanine (FIG. 1B).

The reaction scheme depicted in FIG. 1A is merely one exemplary embodiment. For example, other fluorinated phthalonitriles could be used, as well as other phthalonitriles containing potentially reactive functional groups (eg. —NH$_2$, —N$_3$, —COCl, —CONHNH$_2$) expanding the scope of functionalized fluorine containing-Pcs. The reactive functional group such as the carboxylic acid, can be used for conjugation with a targeting ligand, such as a CTL. Further, anhydrides and other Pc precursors known in the art could serve the same purpose.

Example 2

Synthesis and Characterization of a CTL-Functionalized Fluorine Containing Phthalocyanine A CTP-functionalized fluorine containing phthalocyanine molecule (FIG. 2A) was produced by combining the phthalocyanine molecule of Example 1, (3 eq) with the peptide-bound resin (0.1 mmol), a coupling reagent (HCTU, 3 eq) suspended in DMF (3 mL), and a base (NMM, 6 eq) to initiate the reaction. The reaction proceeded to completion at room temperature on an overhead shaker for 24 h. The resultant mixture was filtered, and the resin was washed successively with DMF (3×10 mL), MeCN (3×10 mL), THF (3×10 mL) and DCM (3×10 mL) and dried in-vacuo. The peptide-bound resin, now coupled to the phthalocyanine molecule, was cleaved from the resin and the side chain protecting groups were deprotected using TFA:H$_2$O:TES (1 mL, 95:2.5:2.5 v/v/v) for 3 h at room temperature. The solution was filtered, concentrated under a stream of air and a solid was precipitated from the solution and washed with cold ether (3×10 mL). The solid was dissolved in MeOH, analyzed and purified by reverse-phase HPLC. The CTP-functionalized fluorine containing-Pc was isolated in about 15% yield and purity >95%. FIG. 2B depicts a high resolution mass spectrum of the CTP-functionalized fluorine containing-Pc. The peaks in the mass spectrum indicate the molecular weight of the CTP-functionalized fluorine containing phthalocyanine (FIG. 2B).

Example 3

Synthesis and Characterization of a CTO-Functionalized Fluorine Containing Phthalocyanine A CTO-functionalized fluorine containing phthalocyanine molecule (FIG. 3A) was produced by combining the phthalocyanine molecule of Example 1, (3 eq) with the oligonucleotide-bound resin (1 μmol), a coupling reagent (HCTU, 3 eq) suspended in DMF (1 mL), and a base (NMM, 6 eq) to initiate the reaction. The reaction proceeded overnight to completion at room temperature on an overhead shaker. The mixture was filtered, the resin was washed successively with DMF (3×10 mL), MeCN (3×10 mL), THF (3×10 mL) and DCM (3×10 mL) and dried in-vacuo. The oligonucleotide-bound resin, now coupled to the phthalocyanine molecule, was cleaved from the resin and the oligonucleotide protecting groups were removed using NH$_4$OH:EtOH (1 mL, 3:1 v/v) for 24 h at 55° C. The solution was filtered, concentrated and a solid was precipitated and washed with cold n-BuOH in 3 M NaOAc (1 mL). The solid was dissolved in autoclaved water, analyzed and purified by ion-pairing reverse-phase HPLC. The CTO-functionalized fluorine containing phthalocyanine molecule was isolated in a purity >95%. FIG. 3B depicts a high resolution liquid chromatography-mass spectroscopy (LCMS) spectra of the CTO-functionalized fluorine containing-Pc. The LCMS spectra validates the single peak purity of the sample and confirms the molecular weight of the CTO-functionalized fluorine containing phthalocyanine molecule (FIG. 3B).

Example 4

Optical Properties of a CTO-Functionalized Fluorine Containing Phthalocyanine

FIG. 4A depicts an optical absorption spectrum for the CTO-functionalized fluorine containing-Pc of Example 3. The optical absorption spectrum, shown in the ultraviolet-visible (UV-VIS) region of the electromagnetic spectrum (200-700 nm), was acquired with a dual beam UV-Vis spectrophotometer (Perkin Elmer or Varian Cary 300). The absorption values were obtained for the CTO-functionalized fluorine containing-Pc (10 μM) in a physiologically relevant phosphate buffer (140 mM KCl, 5 mM NaH$_2$PO$_4$, 1 mM MgCl$_2$, pH=7.2). The data was averaged over a range of five different absorbance scans and reported as a mean value with a standard deviation no greater than 0.1 a.u. Characteristic absorptions for the Pc and CTO components of the CTO-functionalized fluorine containing-Pc are found at ~680 nm ~260 nm, respectively.

FIG. 4B depicts a fluorescence emission spectrum for the CTO-functionalized fluorine containing-Pc of Example 3. The fluorescence emission spectrum was obtained using a FLUOROLOG-3 spectrofluorometer (Horiba Jobin Y von, Edison, N.J.). The spectrofluorometer was equipped with a 450 W xenon lamp and a cooled Hamamatsu R928 photomultiplier operated at 900 V in the photon-counting mode. To obtain the fluorescence spectrum, the sample was excited at a wavelength of 687 nm and emission was monitored at 677 nm.

Example 5

Binding Properties of a CTO-Functionalized Fluorine Containing Phthalocyanine

The propensity for the CTO of the CTO-functionalized fluorine containing-Pc of Example 3 to hybridize to a target oligonucleotide sequence was assessed by thermal denaturation studies. In this exemplary embodiment, the CTO (5'-CTTCATCTTGCCGGCGCT-3' (SEQ ID NO: 16)) is a ligand that targets complementary DNA (3'-GAAGTA-GAACGGCCGCGA-5' (SEQ ID NO: 42)) and RNA (3'-GAAGUAGAACGGCCGCGA-5' (SEQ ID NO: 43)) sequences of the oncogene that expresses GRP78. The DNA and RNA sequences were hybridized with the CTO in a physiologically relevant phosphate buffer (140 mM KCl, 5 mM NaH$_2$PO$_4$, 1 mM MgCl$_2$, pH=7.2). The solutions were denatured at 95° C. for 1 min then cooled to room temperature over 2.5 h and kept at 4° C. overnight prior to conducting thermal denaturation.

Thermal denaturation was determined by monitoring the optical absorption peak of the CTO (~260 nm) as a function of temperature. Optical absorption was performed on a Varian UV-Vis Cary 300 dual beam spectrophotometer equipped with a temperature controller. The thermal melts were run from 5-90° C. with temperature gradient increments of 0.5° C./min and data points collected every 0.5° C./min at ~260 nm. Melting points (T$_m$) for denaturation of CTO:DNA and CTO:RNA hybridized sequences were determined for a CTO coupled to a Pc (experimental) and for the control samples. These results are tabulated in Table 3. The T$_m$ was calculated according to the temperature at which 50% of the duplex denatured to single strands from a plot comparing the changes in sample absorption vs temperature. In this plot, duplexes formed in between the Pc-CTO:DNA and Pc-CTO:RNA held similar melting points (T$_m$~72-75° C.) relative to the control DNA and DNA:RNA duplexes (T$_m$~72-73° C.). This data validates the oncogene targeting capabilities of the CTO that is largely unaffected by the Pc component.

TABLE 3

Melting temperatures, T$_m$ (° C.), for hybridized Pc-CTO:DNA and Pc-CTO:RNA.

| Example | Sequence | T$_m$ |
|---|---|---|
| Pc-CTO:DNA | F$_{48}$H$_7$PcZn—CONH—C6-5'-CTTCATCTTGCCGGC GCT-3' (SEQ ID NO: 16) 3'-GAAGTAGAACGGCCGCGA-5' (SEQ ID NO: 42) | 75 |
| Pc-CTO:RNA | F$_{48}$H$_7$PcZn—CONH—C6-5'-CTTCATCTTGCCGGC GCT-3' (SEQ ID NO: 16) 3'-GAAGUAGAACGGCCGCGA-5' (SEQ ID NO: 43) | 72 |
| CTO:DNA | 5'-CTTCATCTTGCCGGCGCT-3' (SEQ ID NO: 16) 3'-GAAGTAGAACGGCCGCGA-5' (SEQ ID NO: 42) | 73 |
| CTO:RNA | 5'-CTTCATCTTGCCGGCGCT-3' (SEQ ID NO: 16) 3'-GAAGUAGAACGGCCGCGA-5' (SEQ ID NO: 43) | 74 |

Example 6

Photo-Oxidation and Cleavage Activity of CTO-Functionalized Fluorine Containing Phthalocyanine The Pc-CTO:DNA and Pc-CTO:RNA of Example 5 (6.7 μM) were annealed in a physiological phosphate binding buffer (140 mM KCl, 1 mM MgCl$_2$, 5 mM Na$_2$PHO$_4$ adjusted to pH 7.2). The control samples, CTO:DNA and CTO:RNA, were also annealed in the same buffer. In the photo-oxidation reaction, air was passed inside the microtube reactor (1 mL) containing the duplex sequences in buffer to saturate the solution with oxygen. The photo-oxidation reaction, whereby the Pc is illuminated to catalyze the formation of ROS, was then initiated by shining light (>250000 Lux) onto the samples at room temperature (about 22° C.). Aliquots (7 µL), collected at different time points (0-12 h) during the illumination process, were transferred to separately sealed microtubes and stored in the absence of light at 4° C. until further use.

The aliquots were then dissolved in 1 M piperidine in water (150 µL, pH 12) and incubated for 45 min at 95° C. These reaction conditions have been shown to fragment oligonucleotides selectively at oxidized sites [Burrows, C. J. et. al. (1998) Oxidative Nucleobase Modifications Leading to Strand Scission, Chem. Rev. 98, 1109-1152]. The resulting solutions were then centrifuged and concentrated to dryness on a Savant speedvac concentrator.

The resulting products were analyzed using polyacrylimide gel electrophoresis (PAGE). The resulting products were then re-suspended using 80% formamide in autoclaved water (10 µL) and loaded on a 24% denaturing (7 M urea) polyacrylimide gel, as shown in FIGS. 5A and 5B for Pc-CTO:DNA and Pc-CTO:RNA, respectively. Lane 1 of each gel was filled with an experimental or control sample that was not reacted as discussed above. Thus, this sample was not saturated with oxygen nor illuminated with light. Lane 2 of the gel was filled with an experimental or control sample that was saturated with oxygen, but was not illuminated. The remaining lanes of the gel were filled with samples that were both saturated with oxygen and illuminated over the time periods discussed herein. Following electrophoresis, the gel was visualized under short-UV shadowing (265 nm) and subsequently placed in a Stains-All® (Sigma) dye solution (25 mg Stains-All®, 50 mL isopropyl alcohol, 25 mL formamide, 125 mL water) for visualizing the resolved bands. As shown for the Pc-CTO:DNA (FIG. 5A) and Pc-CTO:RNA (FIG. 5B), fragmentation patterns were clearly observed in lanes 3-13 where samples were both saturated with oxygen and illuminated. In contrast, the control samples, CTO:DNA and CTO:RNA did not exhibit any fragmentation under the same experimental conditions. These results validate the ability for the Pc-CTO to produce singlet oxygen for the oxidation of the GRP78 oncogenes. This photo-oxidation reaction renders the oligonucleotides susceptible to fragmentation at oxidized sites with the hot piperidine treatment. In-vivo, repair enzymes such as formamidopyrimidine [fapy]-DNA glycosylase (Fpg) are known to degrade oligonucleotides at oxidized sites rendering this discovery applicable to an oncogene-targeting PDT approach [Tchou, J. et. al. (1994) Substrate specificity of Fpg protein. Recognition and cleavage of oxidatively damaged DNA, J. Biol. Chem. 269, 15318-15324].

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention described herein has been described with reference to particular embodiments, it is to be understood that these embodiments are merely illustrative of the principle and applications described herein. It is therefore to be understood that numerous modifications may be made to the illustrative embodiments and that other arrangements may be devised without departing from the spirit and scope of the various embodiments described herein as defined by the amended claims.

The invention claimed is:

1. A functionalized fluorine containing phthalocyanine represented by Formula (I):

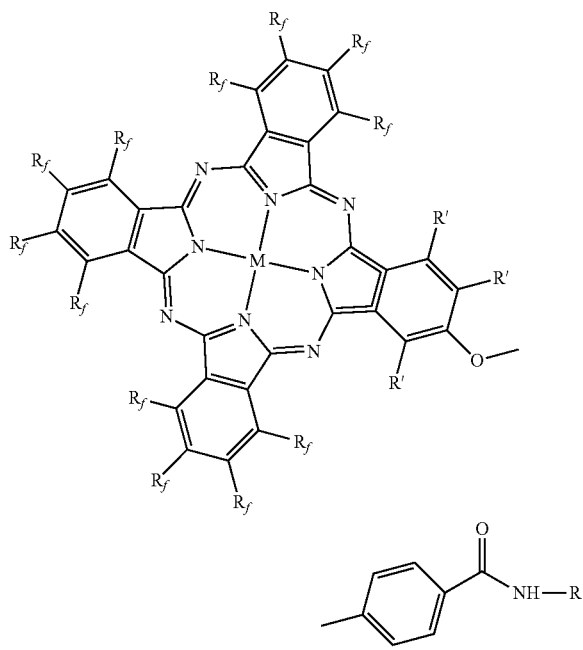

Formula (I)

wherein each $R_f$ is independently selected from the group consisting of —C(CF$_3$)$_2$F and a fluorine atom (—F),
wherein at least one $R_f$ includes a fluorine atom,
wherein each R' is a hydrogen atom,
wherein M is selected from the group consisting of Zn$^{2+}$, Mg$^{2+}$, low-spin Fe$^{2+}$, Ru$^{2+}$, Pt$^{2+}$, Ti$^{4+}$, Si$^{4+}$, and two protons (H$^+$), and wherein R includes at least one ligand selected from the group consisting of a peptide selected from SEQ ID NO: 17-41, and an oligonucleotide selected from SEQ ID NO: 1-16.

2. The functionalized fluorine containing phthalocyanine of claim 1, wherein R includes at least one ligand that is an oligonucleotide selected from SEQ ID NO: 1-16, and further comprising:
a second oligonucleotide, wherein
the second oligonucleotide is complementary to the oligonucleotide selected from SEQ ID NO: 1-16.

3. A pharmaceutical composition including the functionalized fluorine containing phthalocyanine of claim 1 and a pharmaceutical acceptable carrier.

4. The pharmaceutical composition of claim 3, wherein R includes at least one ligand that is an oligonucleotide selected from SEQ ID NO: 1-16, and wherein the fluorine containing phthalocyanine further comprises:
a second oligonucleotide, wherein
the second oligonucleotide is complementary to the oligonucleotide selected from SEQ ID NO: 1-16.

5. The functionalized fluorine containing phthalocyanine of claim 1, wherein the at least one ligand is an oligonucleotide selected from SEQ ID NO: 1-16, and wherein R further comprises —(CH$_2$)$_6$—.

6. The functionalized fluorine containing phthalocyanine of claim 5, wherein the at least one ligand is an oligonucleotide of SEQ ID NO: 16, and wherein M is Zn$^{2+}$.

7. The functionalized fluorine containing phthalocyanine of claim 1, wherein the at least one ligand is an oligonucleotide of SEQ ID NO: 16, and wherein M is Zn$^{2+}$.

8. The pharmaceutical composition of claim 7, wherein the fluorine containing phthalocyanine further comprises:
a second oligonucleotide, wherein
the second oligonucleotide is complementary to the oligonucleotide selected from SEQ ID NO: 1-16.

9. A pharmaceutical composition including the functionalized fluorine containing phthalocyanine of claim 8 and a pharmaceutical acceptable carrier.

* * * * *

SEQUENCE LISTING

```
<160> NUMBER OF SEQ ID NOS: 43

<210> SEQ ID NO 1
<211> LENGTH: 24
<212> TYPE: RNA
<213> ORGANISM: Oncorhynchus mykiss

<400> SEQUENCE: 1
aaggaugguu aaugaugcug agaa                                          24

<210> SEQ ID NO 2
<211> LENGTH: 24
<212> TYPE: RNA
<213> ORGANISM: Oncorhynchus mykiss

<400> SEQUENCE: 2
uucucagcau cauuaaccau ccuu                                          24

<210> SEQ ID NO 3
<211> LENGTH: 21
<212> TYPE: DNA
<213> ORGANISM: Oncorhynchus mykiss
<220> FEATURE:
<223> OTHER INFORMATION: Description of Combined DNA/RNA Molecule:
      Oligonucleotide

<400> SEQUENCE: 3
ggagcgcauu gauacuagat t                                             21

<210> SEQ ID NO 4
```

```
<211> LENGTH: 21
<212> TYPE: DNA
<213> ORGANISM: Oncorhynchus mykiss
<220> FEATURE:
<223> OTHER INFORMATION: Description of Combined DNA/RNA Molecule:
      Oligonucleotide

<400> SEQUENCE: 4
ucuaguauca augcgcucct t                                               21

<210> SEQ ID NO 5
<211> LENGTH: 21
<212> TYPE: RNA
<213> ORGANISM: Oncorhynchus mykiss

<400> SEQUENCE: 5
aagaaaagcu gggagguaaa c                                               21

<210> SEQ ID NO 6
<211> LENGTH: 21
<212> TYPE: RNA
<213> ORGANISM: Oncorhynchus mykiss

<400> SEQUENCE: 6
guuuaccucc cagcuuuucu u                                               21

<210> SEQ ID NO 7
<211> LENGTH: 21
<212> TYPE: RNA
<213> ORGANISM: Oncorhynchus mykiss

<400> SEQUENCE: 7
aagaaaagcu gggagguaaa c                                               21

<210> SEQ ID NO 8
<211> LENGTH: 21
<212> TYPE: RNA
<213> ORGANISM: Oncorhynchus mykiss

<400> SEQUENCE: 8
aacaacugca uggguaaccu u                                               21

<210> SEQ ID NO 9
<211> LENGTH: 21
<212> TYPE: DNA
<213> ORGANISM: Oncorhynchus mykiss
<220> FEATURE:
<223> OTHER INFORMATION: Description of Combined DNA/RNA Molecule:
      Oligonucleotide

<400> SEQUENCE: 9
ggagcgcauu gauacuagat t                                               21

<210> SEQ ID NO 10
<211> LENGTH: 21
<212> TYPE: DNA
<213> ORGANISM: Oncorhynchus mykiss
<220> FEATURE:
<223> OTHER INFORMATION: Description of Combined DNA/RNA Molecule:
      Oligonucleotide

<400> SEQUENCE: 10
ucuaguauca augcgcucct t                                               21

<210> SEQ ID NO 11
```

```
<211> LENGTH: 25
<212> TYPE: RNA
<213> ORGANISM: Oncorhynchus mykiss

<400> SEQUENCE: 11
cgagugacag cugaagacaa gggua                                              25

<210> SEQ ID NO 12
<211> LENGTH: 25
<212> TYPE: RNA
<213> ORGANISM: Oncorhynchus mykiss

<400> SEQUENCE: 12
uacccuuguc uucagcuguc acucg                                              25

<210> SEQ ID NO 13
<211> LENGTH: 19
<212> TYPE: RNA
<213> ORGANISM: Oncorhynchus mykiss

<400> SEQUENCE: 13
aguguuggaa gauucugau                                                     19

<210> SEQ ID NO 14
<211> LENGTH: 19
<212> TYPE: RNA
<213> ORGANISM: Oncorhynchus mykiss

<400> SEQUENCE: 14
aucagaaucu uccaacacu                                                     19

<210> SEQ ID NO 15
<211> LENGTH: 19
<212> TYPE: RNA
<213> ORGANISM: Oncorhynchus mykiss

<400> SEQUENCE: 15
ggagcgcauu gauacuaga                                                     19

<210> SEQ ID NO 16
<211> LENGTH: 18
<212> TYPE: DNA
<213> ORGANISM: Oncorhynchus mykiss

<400> SEQUENCE: 16
cttcatcttg ccggcgct                                                      18

<210> SEQ ID NO 17
<211> LENGTH: 13
<212> TYPE: PRT
<213> ORGANISM: Oncorhynchus mykiss

<400> SEQUENCE: 17

Cys Thr Val Ala Leu Pro Gly Gly Tyr Val Arg Val Cys
1               5                   10

<210> SEQ ID NO 18
<211> LENGTH: 7
<212> TYPE: PRT
<213> ORGANISM: Oncorhynchus mykiss

<400> SEQUENCE: 18

Ala Ser Ser Leu Asn Ile Ala
1               5
```

```
<210> SEQ ID NO 19
<211> LENGTH: 14
<212> TYPE: PRT
<213> ORGANISM: Oncorhynchus mykiss

<400> SEQUENCE: 19

Gln Pro Phe Met Gln Cys Leu Cys Ile Tyr Asp Ala Ser Cys
1               5                   10

<210> SEQ ID NO 20
<211> LENGTH: 8
<212> TYPE: PRT
<213> ORGANISM: Oncorhynchus mykiss
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (6)..(7)
<223> OTHER INFORMATION: Any amino acid

<400> SEQUENCE: 20

Xaa Leu Trp Leu Leu Xaa Xaa Gly
1               5

<210> SEQ ID NO 21
<211> LENGTH: 7
<212> TYPE: PRT
<213> ORGANISM: Oncorhynchus mykiss

<400> SEQUENCE: 21

Ser Phe Thr Tyr Trp Thr Asn
1               5

<210> SEQ ID NO 22
<211> LENGTH: 9
<212> TYPE: PRT
<213> ORGANISM: Oncorhynchus mykiss

<400> SEQUENCE: 22

Cys Lys Ser Thr His Asp Arg Leu Cys
1               5

<210> SEQ ID NO 23
<211> LENGTH: 5
<212> TYPE: PRT
<213> ORGANISM: Oncorhynchus mykiss
<220> FEATURE:
<221> NAME/KEY: MOD_RES
<222> LOCATION: (1)..(1)
<223> OTHER INFORMATION: Ile or Leu

<400> SEQUENCE: 23

Xaa Gly Ser Gly Leu
1               5

<210> SEQ ID NO 24
<211> LENGTH: 9
<212> TYPE: PRT
<213> ORGANISM: Oncorhynchus mykiss

<400> SEQUENCE: 24

Cys Val Ser Asn Pro Arg Trp Lys Cys
1               5
```

```
<210> SEQ ID NO 25
<211> LENGTH: 20
<212> TYPE: PRT
<213> ORGANISM: Oncorhynchus mykiss

<400> SEQUENCE: 25

Trp Leu Ser Glu Ala Gly Pro Val Val Thr Val Arg Ala Leu Arg Gly
1               5                   10                  15
Thr Gly Ser Trp
            20

<210> SEQ ID NO 26
<211> LENGTH: 10
<212> TYPE: PRT
<213> ORGANISM: Oncorhynchus mykiss

<400> SEQUENCE: 26

Cys Gly Leu Ile Ile Gln Lys Asn Glu Cys
1               5                   10

<210> SEQ ID NO 27
<211> LENGTH: 3
<212> TYPE: PRT
<213> ORGANISM: Oncorhynchus mykiss

<400> SEQUENCE: 27

Pro Arg Pro
1

<210> SEQ ID NO 28
<211> LENGTH: 20
<212> TYPE: PRT
<213> ORGANISM: Oncorhynchus mykiss

<400> SEQUENCE: 28

Arg Gly Asp Leu Ala Thr Leu Arg Gln Leu Ala Gln Glu Asp Gly Val
1               5                   10                  15
Val Gly Val Arg
            20

<210> SEQ ID NO 29
<211> LENGTH: 9
<212> TYPE: PRT
<213> ORGANISM: Oncorhynchus mykiss
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 29

Cys Xaa Asn Xaa Asp Xaa Arg Xaa Cys
1               5

<210> SEQ ID NO 30
```

-continued

```
<211> LENGTH: 5
<212> TYPE: PRT
<213> ORGANISM: Oncorhynchus mykiss

<400> SEQUENCE: 30

Cys Gly Lys Arg Lys
1               5

<210> SEQ ID NO 31
<211> LENGTH: 7
<212> TYPE: PRT
<213> ORGANISM: Oncorhynchus mykiss

<400> SEQUENCE: 31

His Thr Phe Glu Pro Gly Val
1               5

<210> SEQ ID NO 32
<211> LENGTH: 12
<212> TYPE: PRT
<213> ORGANISM: Oncorhynchus mykiss

<400> SEQUENCE: 32

Val Pro Trp Met Glu Pro Ala Tyr Gln Arg Phe Leu
1               5                   10

<210> SEQ ID NO 33
<211> LENGTH: 7
<212> TYPE: PRT
<213> ORGANISM: Oncorhynchus mykiss

<400> SEQUENCE: 33

Val His Leu Gly Tyr Ala Thr
1               5

<210> SEQ ID NO 34
<211> LENGTH: 12
<212> TYPE: PRT
<213> ORGANISM: Oncorhynchus mykiss

<400> SEQUENCE: 34

Thr Ala Cys His Gln His Val Arg Met Val Arg Pro
1               5                   10

<210> SEQ ID NO 35
<211> LENGTH: 9
<212> TYPE: PRT
<213> ORGANISM: Oncorhynchus mykiss

<400> SEQUENCE: 35

Leu Val Arg Ser Thr Gly Gln Phe Val
1               5

<210> SEQ ID NO 36
<211> LENGTH: 12
<212> TYPE: PRT
<213> ORGANISM: Oncorhynchus mykiss

<400> SEQUENCE: 36

Thr Ser Pro Leu Asn Ile His Asn Gly Gln Lys Leu
1               5                   10

<210> SEQ ID NO 37
<211> LENGTH: 3
<212> TYPE: PRT
```

```
<213> ORGANISM: Oncorhynchus mykiss

<400> SEQUENCE: 37

Arg Gly Asp
1

<210> SEQ ID NO 38
<211> LENGTH: 9
<212> TYPE: PRT
<213> ORGANISM: Oncorhynchus mykiss

<400> SEQUENCE: 38

Cys Gly Asn Lys Arg Thr Arg Gly Cys
1               5

<210> SEQ ID NO 39
<211> LENGTH: 4
<212> TYPE: PRT
<213> ORGANISM: Oncorhynchus mykiss

<400> SEQUENCE: 39

Arg Trp Ile Asp
1

<210> SEQ ID NO 40
<211> LENGTH: 7
<212> TYPE: PRT
<213> ORGANISM: Oncorhynchus mykiss
<220> FEATURE:
<221> NAME/KEY: MOD_RES
<222> LOCATION: (1)..(1)
<223> OTHER INFORMATION: D-Cys
<220> FEATURE:
<221> NAME/KEY: MOD_RES
<222> LOCATION: (2)..(2)
<223> OTHER INFORMATION: Norleucine
<220> FEATURE:
<221> NAME/KEY: MOD_RES
<222> LOCATION: (3)..(3)
<223> OTHER INFORMATION: D-Cyclohexylglycine
<220> FEATURE:
<221> NAME/KEY: MOD_RES
<222> LOCATION: (7)..(7)
<223> OTHER INFORMATION: D-Cys

<400> SEQUENCE: 40

Cys Xaa Xaa Asn Asp Phe Cys
1               5

<210> SEQ ID NO 41
<211> LENGTH: 7
<212> TYPE: PRT
<213> ORGANISM: Oncorhynchus mykiss
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (2)..(2)
<223> OTHER INFORMATION: D-Tyr
<220> FEATURE:
<221> NAME/KEY: MOD_RES
<222> LOCATION: (3)..(3)
<223> OTHER INFORMATION: D-Pro
<220> FEATURE:
<221> NAME/KEY: MOD_RES
<222> LOCATION: (7)..(7)
<223> OTHER INFORMATION: D-Phe

<400> SEQUENCE: 41
```

```
Phe Tyr Pro Leu Asp Phe Phe
1               5

<210> SEQ ID NO 42
<211> LENGTH: 18
<212> TYPE: DNA
<213> ORGANISM: Oncorhynchus mykiss

<400> SEQUENCE: 42
agcgccggca agatgaag                                              18

<210> SEQ ID NO 43
<211> LENGTH: 18
<212> TYPE: RNA
<213> ORGANISM: Oncorhynchus mykiss

<400> SEQUENCE: 43
agcgccggca agaugaag                                              18
```